United States Patent
Kim et al.

(10) Patent No.: US 10,227,595 B2
(45) Date of Patent: Mar. 12, 2019

(54) UNIVERSAL PROTEIN OVEREXPRESSION TAG COMPRISING RAMP FUNCTION, AND APPLICATION THEREOF

(71) Applicant: INDUSTRY FOUNDATION OF CHONNAM NATIONAL UNIVERSITY, Gwangju (KR)

(72) Inventors: Geun-Joong Kim, Gwanju (KR); Won Ji Park, Gwangju (KR); Sung-Hwan You, Gwangju (KR); Jin-Young Lee, Gwangju (KR); Eun-Bin Lee, Gwangju (KR); Sa-Young Min, Gwangju (KR)

(73) Assignee: INDUSTRY FOUNDATION OF CHONNAM NATIONAL UNIVERSITY, Gwangju (KR)

(*) Notice: Subject to any disclaimer, the term of this patent is extended or adjusted under 35 U.S.C. 154(b) by 246 days.

(21) Appl. No.: 14/773,529

(22) PCT Filed: Feb. 27, 2014

(86) PCT No.: PCT/KR2014/001616
§ 371 (c)(1),
(2) Date: Sep. 8, 2015

(87) PCT Pub. No.: WO2014/142453
PCT Pub. Date: Sep. 18, 2014

(65) Prior Publication Data
US 2016/0017341 A1  Jan. 21, 2016

(30) Foreign Application Priority Data
Mar. 14, 2013  (KR) .................. 10-2013-0027549

(51) Int. Cl.
| | |
|---|---|
| *C12N 15/67* | (2006.01) |
| *C12N 15/70* | (2006.01) |
| *C12P 21/02* | (2006.01) |
| *C07K 1/22* | (2006.01) |
| *C12N 9/10* | (2006.01) |
| *C12N 9/86* | (2006.01) |
| *C12N 9/90* | (2006.01) |
| *C12P 21/00* | (2006.01) |

(52) U.S. Cl.
CPC ................ *C12N 15/67* (2013.01); *C07K 1/22* (2013.01); *C12N 9/1022* (2013.01); *C12N 9/86* (2013.01); *C12N 9/90* (2013.01); *C12N 15/70* (2013.01); *C12P 21/00* (2013.01); *C12P 21/02* (2013.01); *C12Y 202/01007* (2013.01); *C12Y 305/02006* (2013.01); *C12Y 503/03002* (2013.01)

(58) Field of Classification Search
None
See application file for complete search history.

(56) References Cited

U.S. PATENT DOCUMENTS

| | | | |
|---|---|---|---|
| 2006/0099710 A1 | 5/2006 | Donnelly et al. | |
| 2012/0214203 A1 | 8/2012 | Clarke | |

FOREIGN PATENT DOCUMENTS

| | | |
|---|---|---|
| KR | 10-2009-0018799 A | 2/2009 |
| KR | 10-2012-0041245 A | 4/2012 |
| WO | 2010/001414 A1 | 1/2010 |

OTHER PUBLICATIONS

Deepa Agashe, et al., "Good Codons, Bad Transcript: Large Reductions in Gene Expression and Fitness Arising from Synonymous Mutations in a Key-Enzyme", Molecular Biology and Evolution, Dec. 4, 2012, pp. 549-560, vol. 30, No. 3.
Robert Novy, et al., "Overcoming the codon bias of *E. coli* for enhanced protein expression", inNovations, Jun. 2001, pp. 1-3, No. 12.
Sivan Navon, et al., "The role of codon selection in regulation of translation efficiency deduced from synthetic libraries", Genome Biology, 2011, pp. 1-10, vol. 12:R12.
Kurt Frederick, et al., How the Sequence of a Gene Can Tune Its Translation, Cell, Apr. 16, 2010, pp. 227-229, vol. 141.
Tamir Tuller, et al., An Evolutionarily Conserved Mechanism for Controlling the Efficiency of Protein Translation, Cell, Apr. 16, 2010, pp. 344-354, vol. 141.
International Searching Authority, International Search Report for PCT/KR2014/001616 dated May 23, 2014 [PCT/ISA/210].

*Primary Examiner* — Nancy A Treptow
(74) *Attorney, Agent, or Firm* — Sughrue Mion, PLLC

(57) ABSTRACT

Provided is a ramp tag capable of solving instability in translation rate resulting from poor compatibility between codons in a foreign gene and a host when expressing a recombinant protein in *E. coli*. Unlike the conventional codon optimization or codon deoptimization method for solving the problem of rare codons, the present invention increases an expression efficiency of a target protein by merely having the ramp tag be fused with a target gene or independently expressed, without changing the original codon sequence, thereby allowing tRNA to be reused. Thus, the present invention provides a novel method for increasing recombinant protein expression which is capable of reducing costs and time in comparison to the codon optimization method that artificially synthesizes DNA sequences. Therefore, it is expected that the method of the present invention will be able to be used in production of high value-added pharmaceuticals or industrial enzymes.

23 Claims, 25 Drawing Sheets
Specification includes a Sequence Listing.

[Fig. 1A]
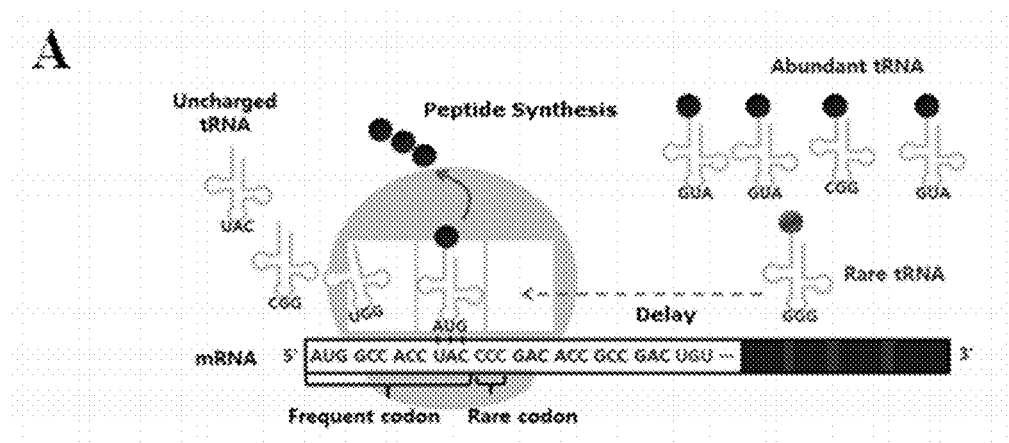
[Fig. 1B]
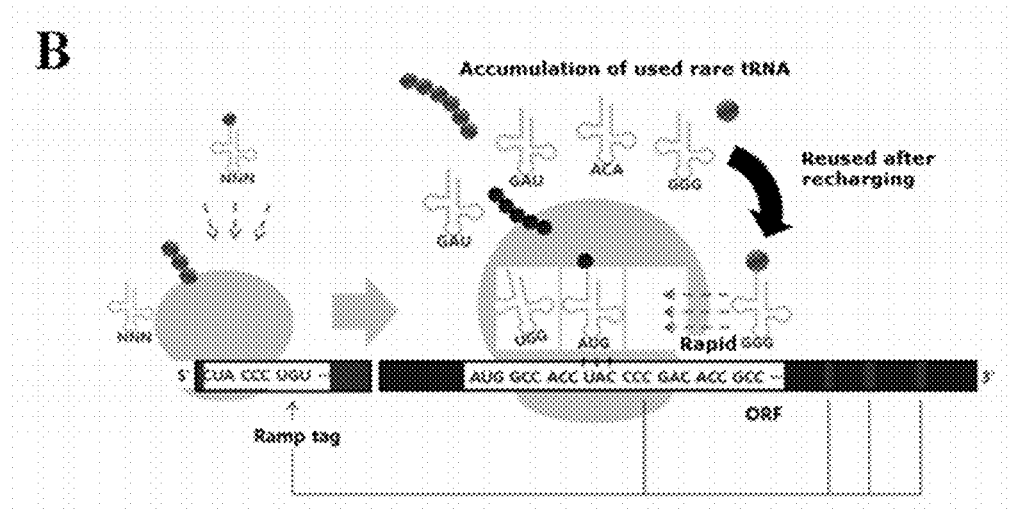

[Fig. 2A]
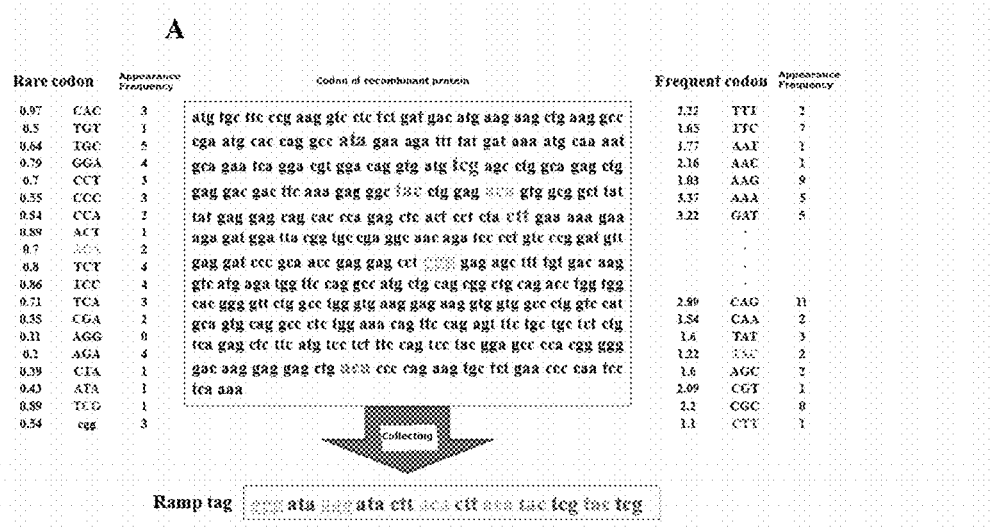
[Fig. 2B]
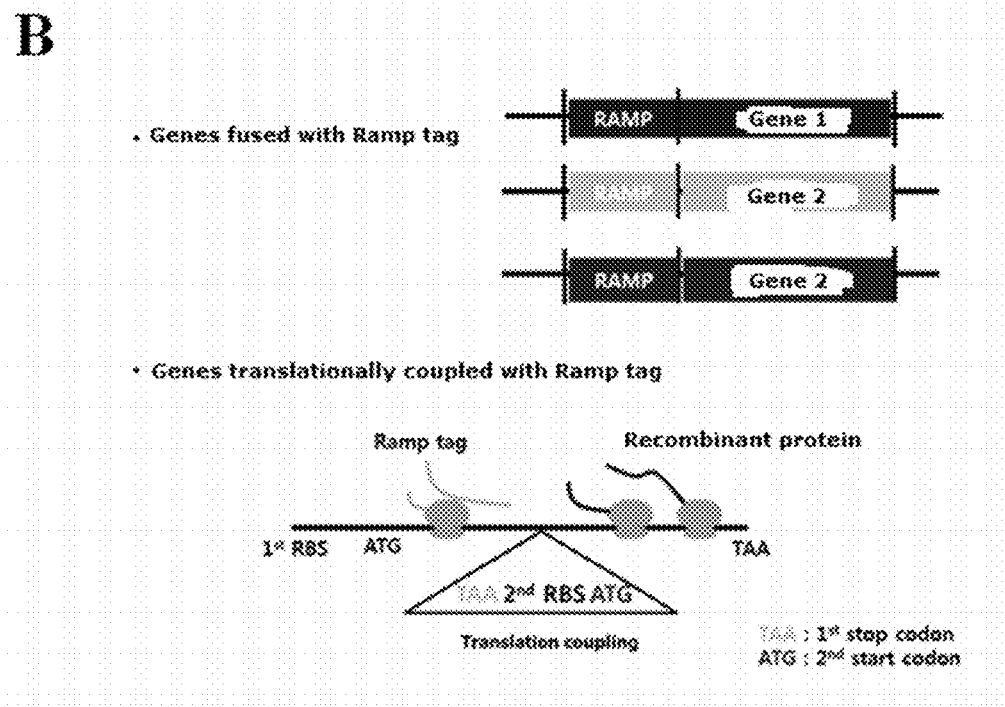

[Fig. 3A]
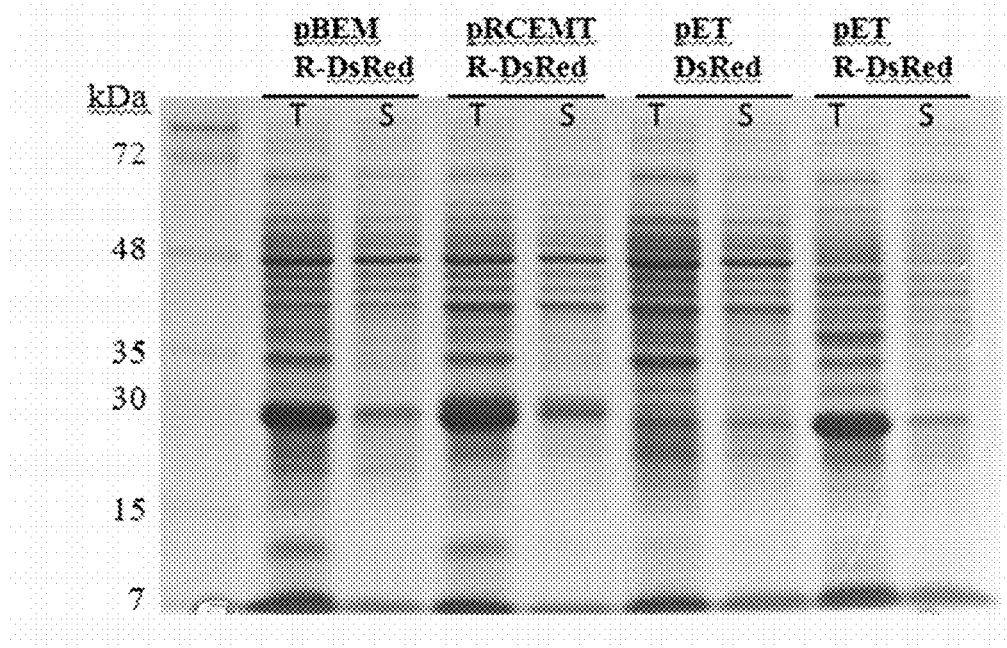
[Fig. 3B]
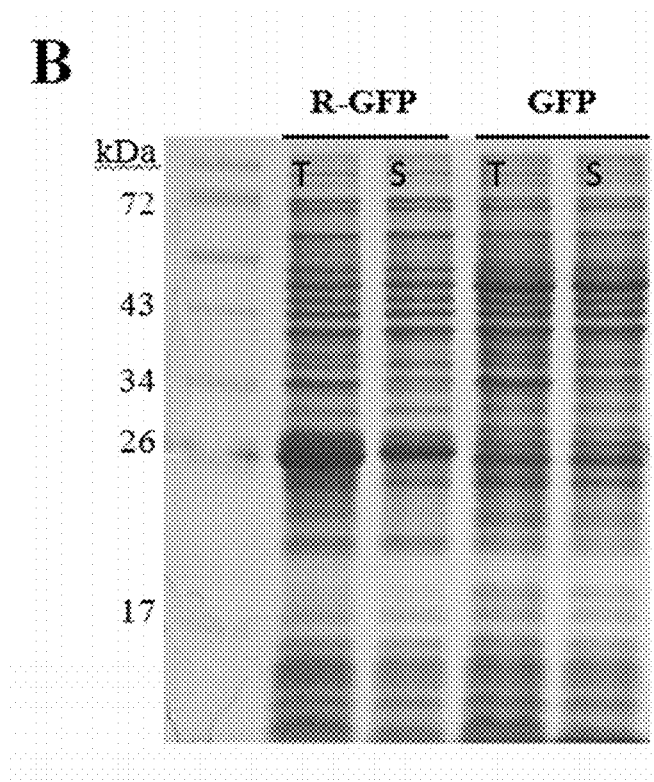

[Fig. 3C]
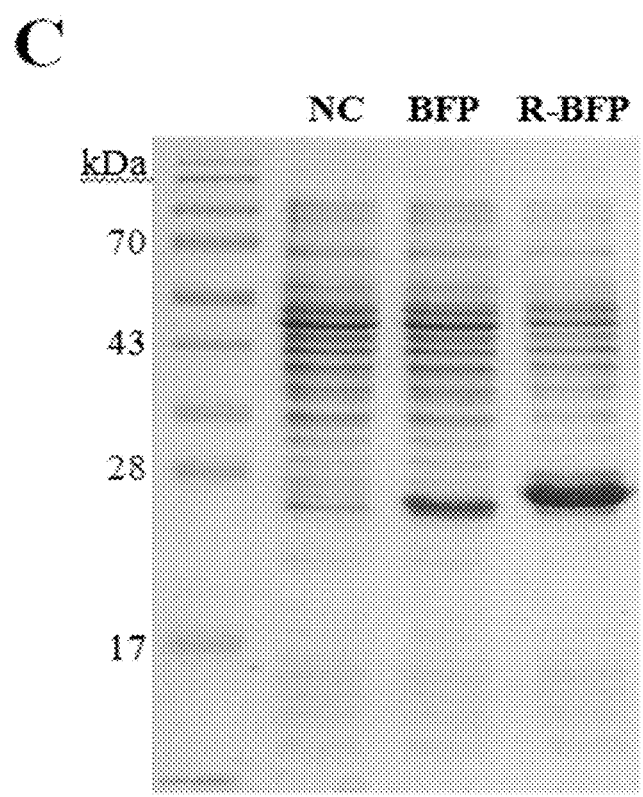

[Fig. 4]
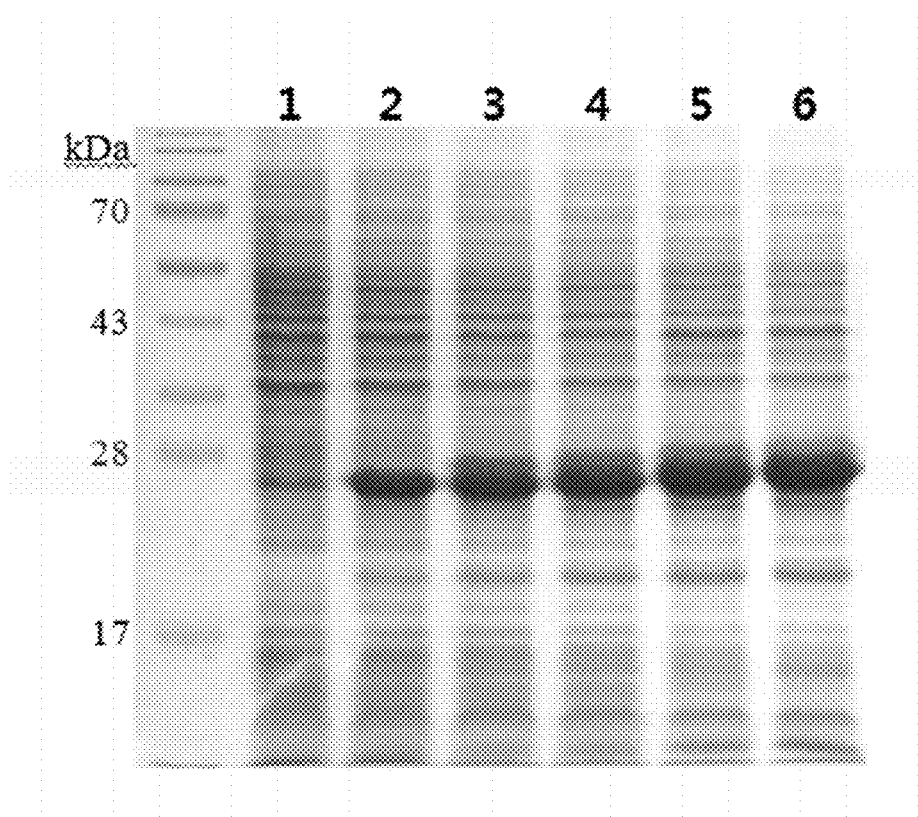

[Fig. 5]
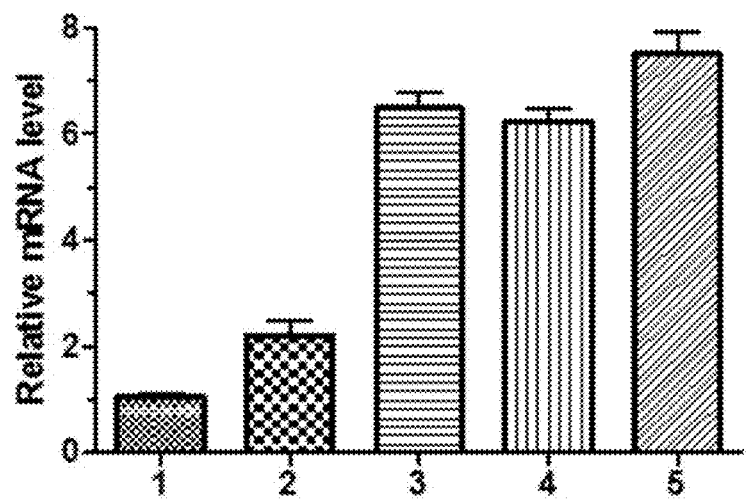

[Fig. 6]
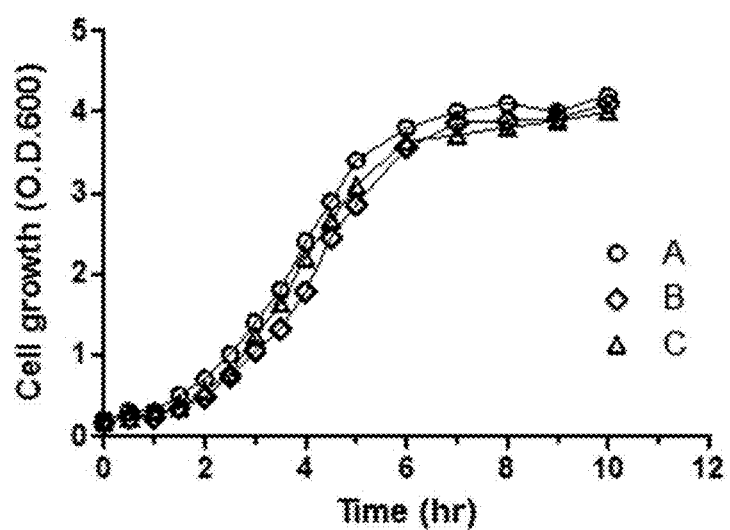

[Fig. 7]
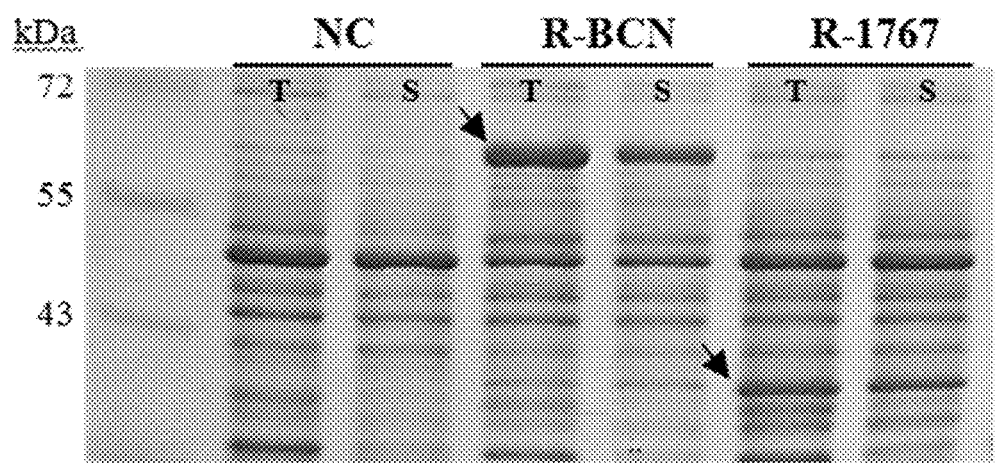

[Fig. 8A]
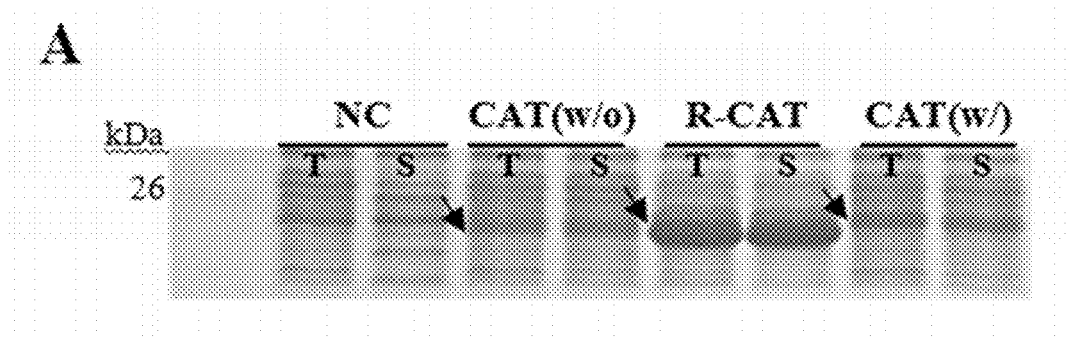
[Fig. 8B]
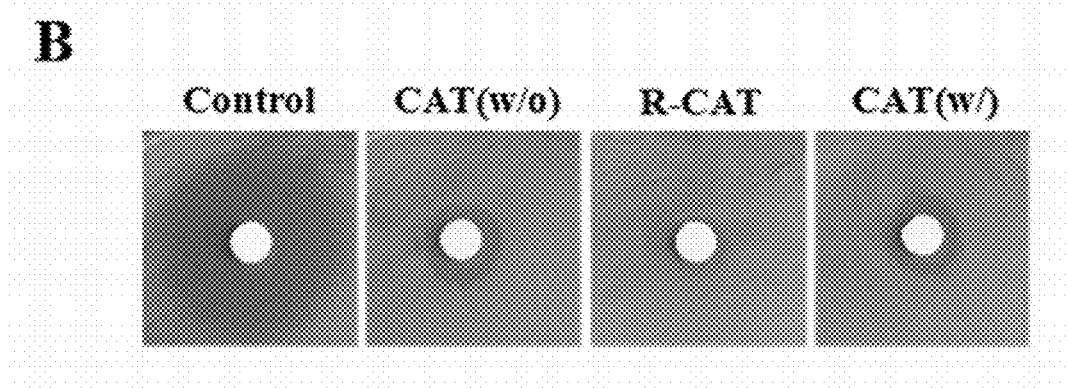

[Fig. 9A]
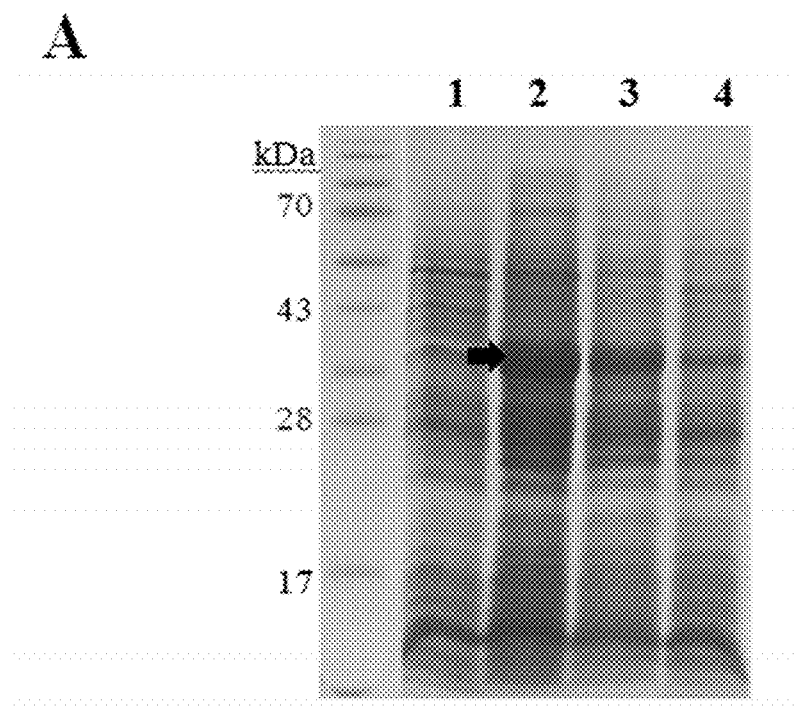
[Fig. 9B]
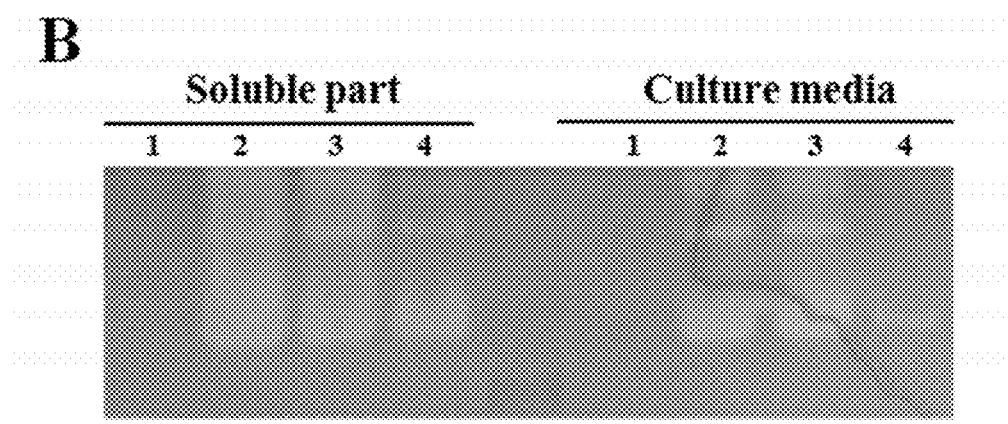

[Fig. 10]
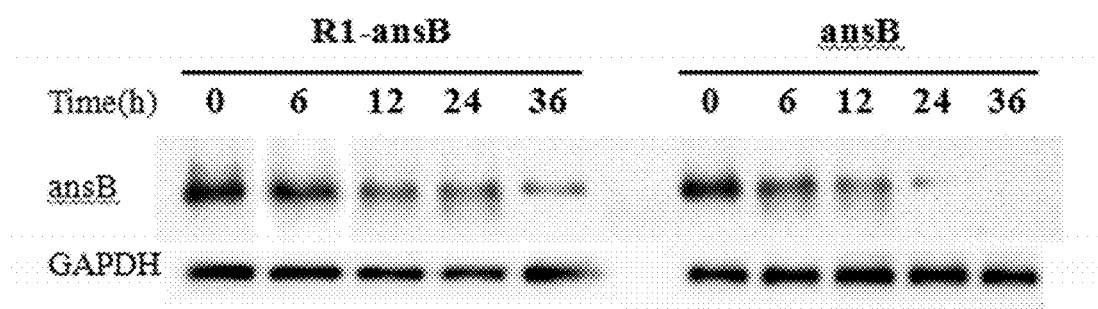

[Fig. 11]
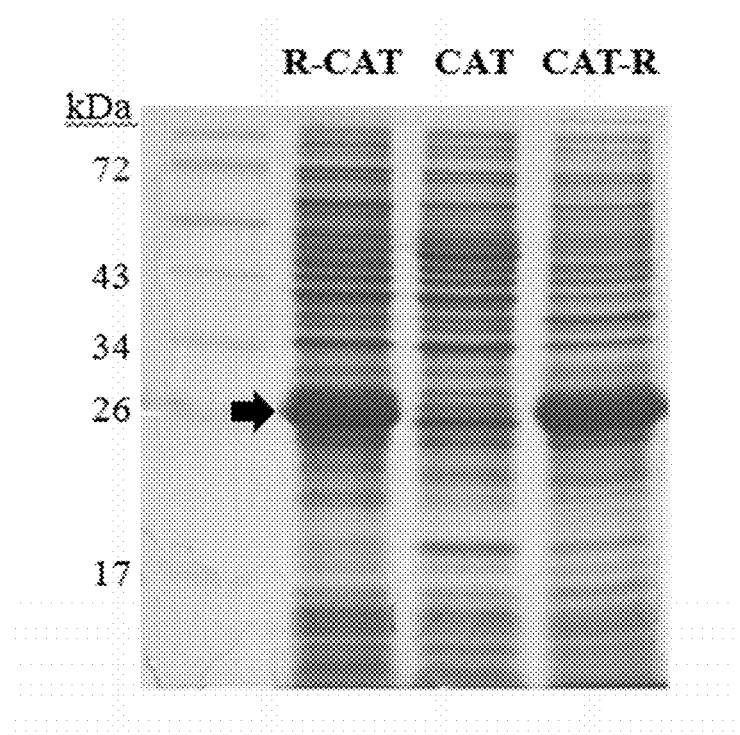

[Fig. 12A]
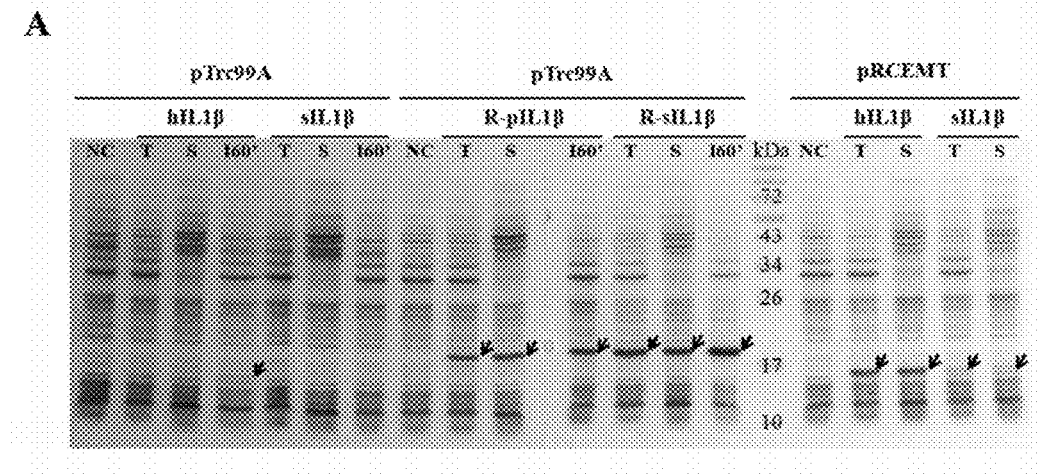
[Fig. 12B]
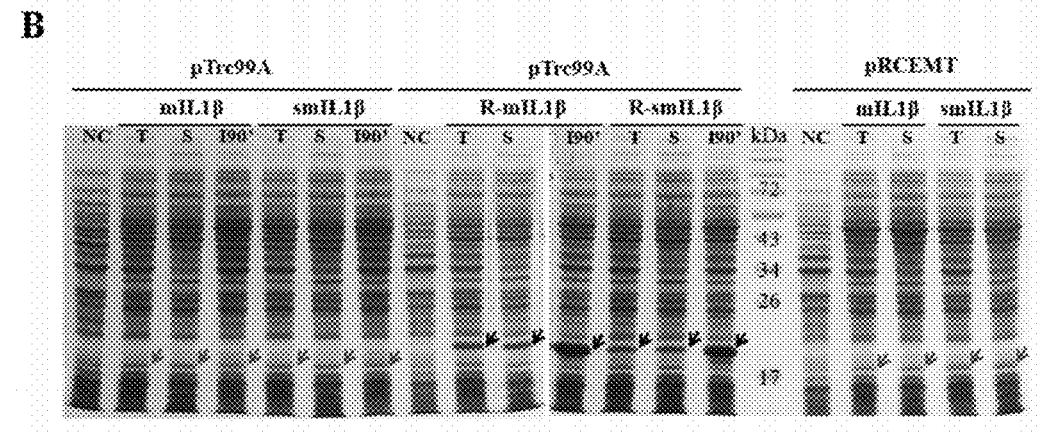

[Fig. 13A]
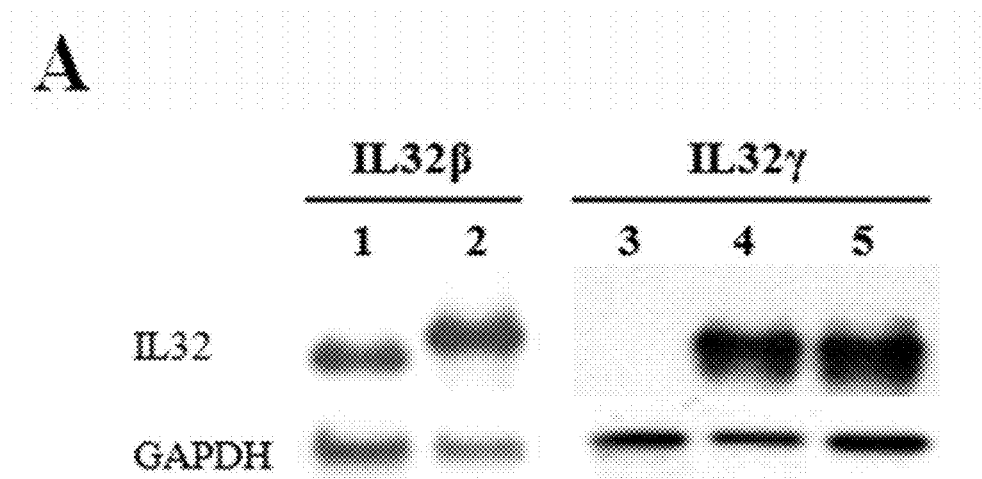
[Fig. 13B]
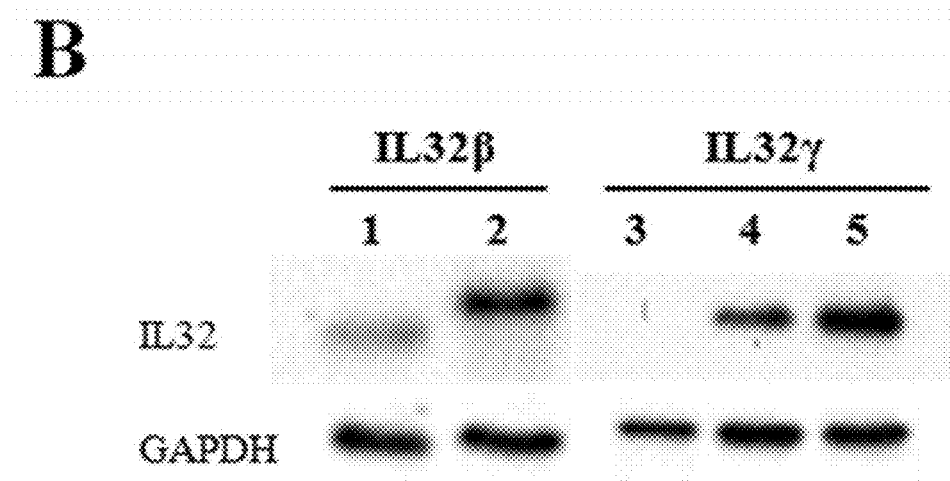

[Fig. 14]
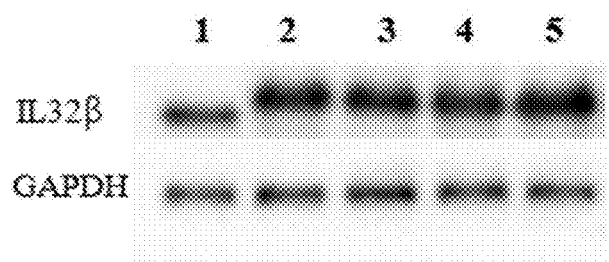

[Fig. 15]
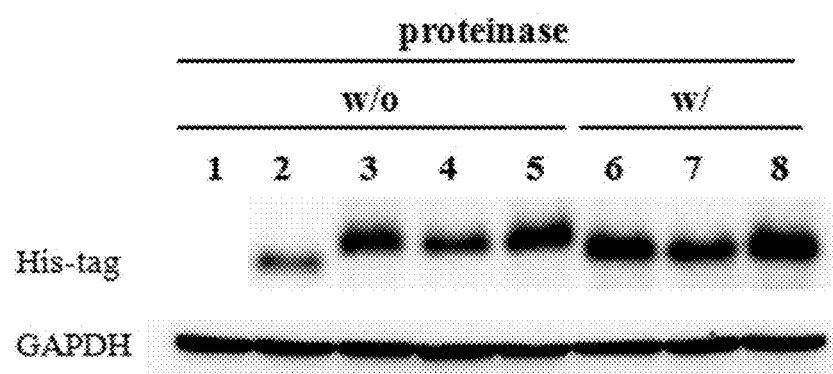

[Fig. 16A]
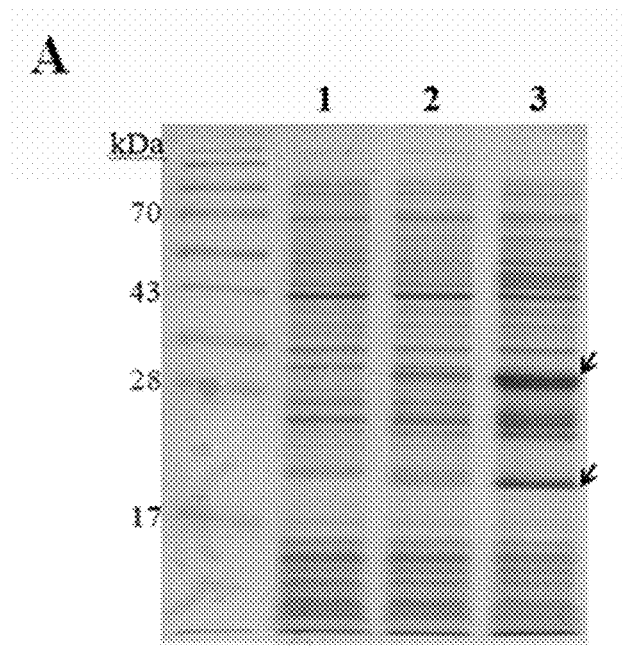
[Fig. 16B]
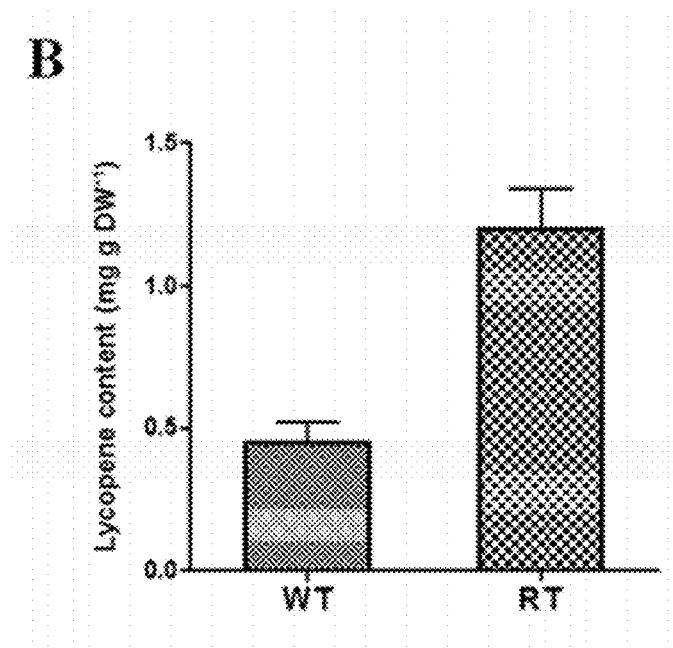

[Fig. 17]
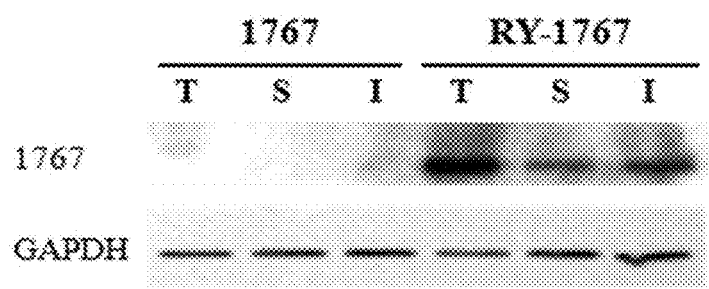

[Fig. 18]
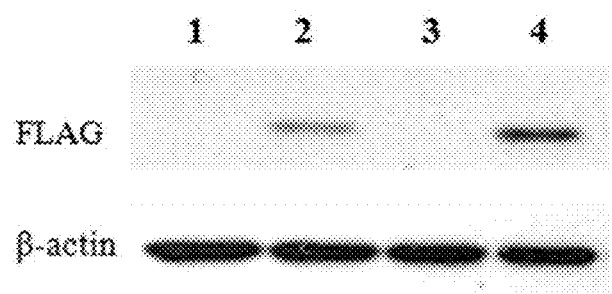

[Fig. 19]
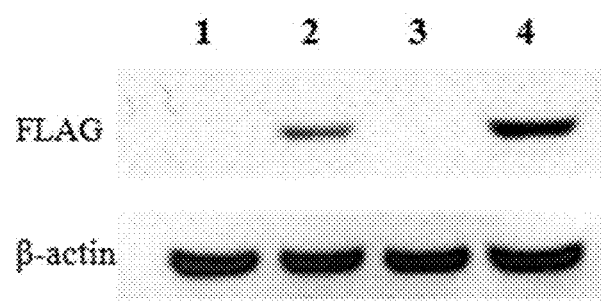

[Fig. 20]
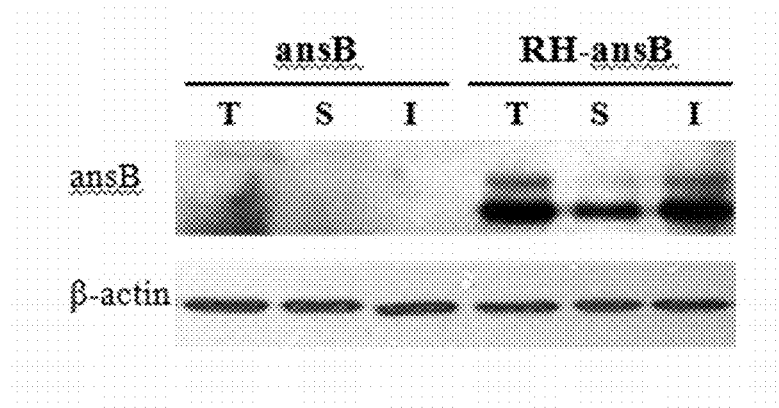

[Fig. 21A]
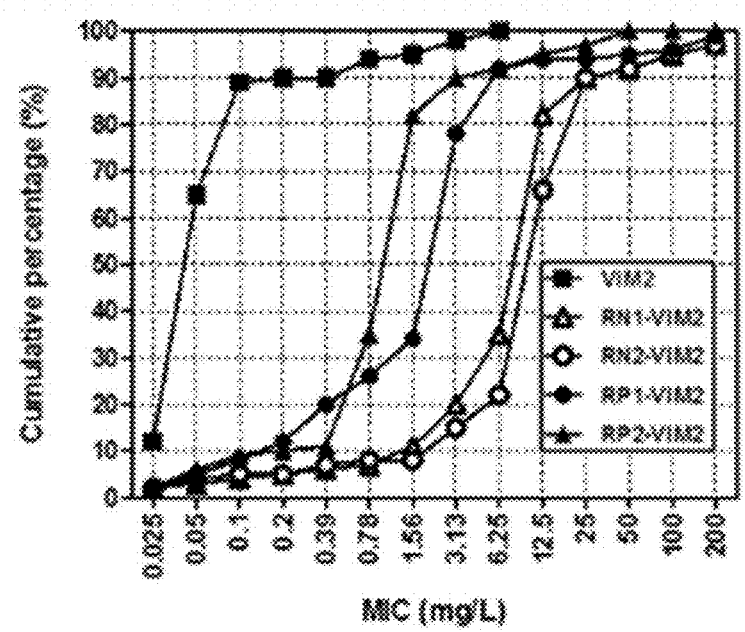
[Fig. 21B]
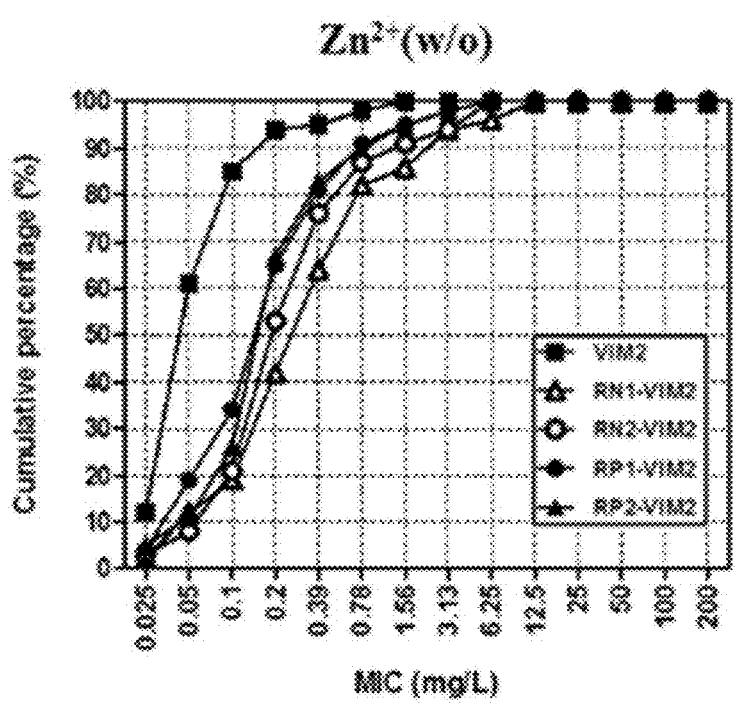

[Fig. 21C]
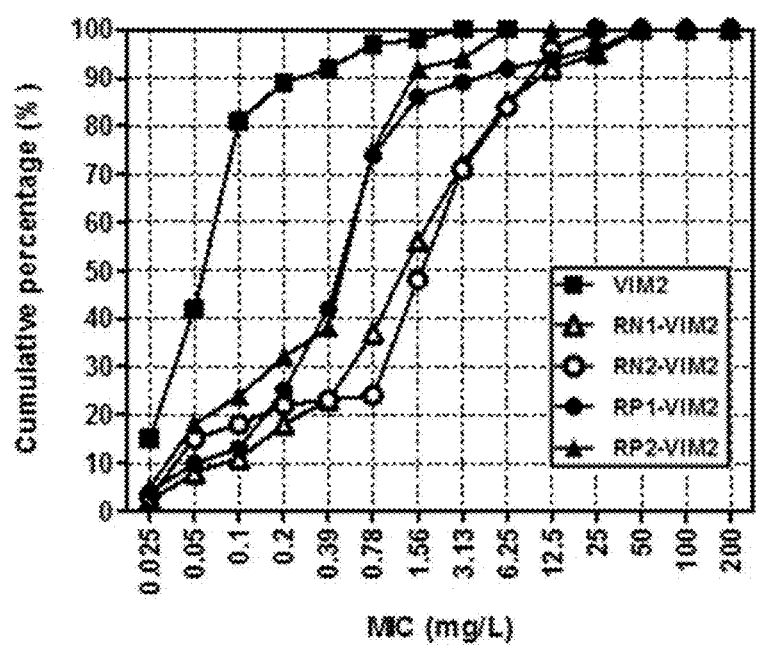

[Fig. 22A]
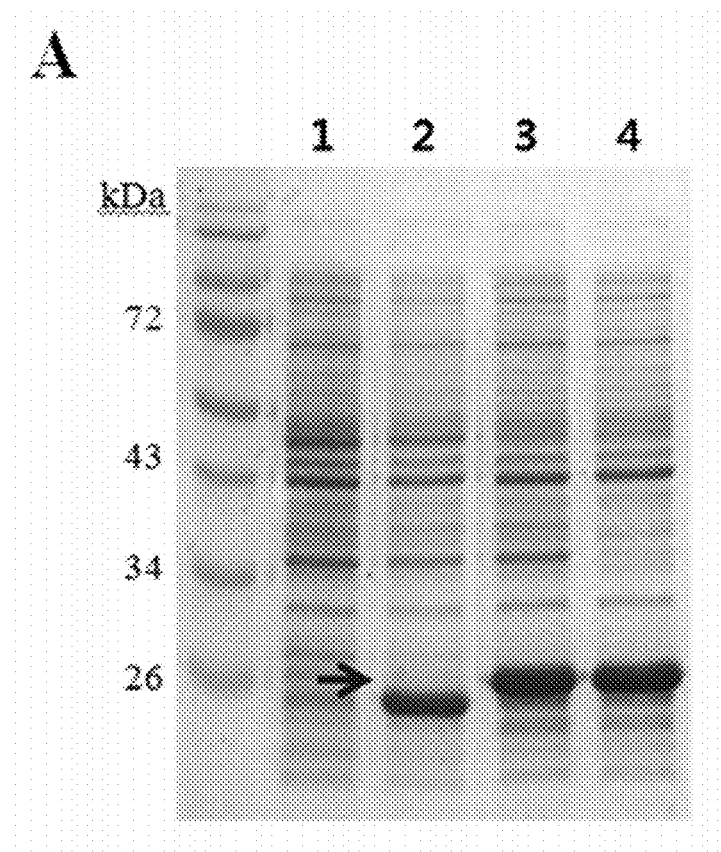

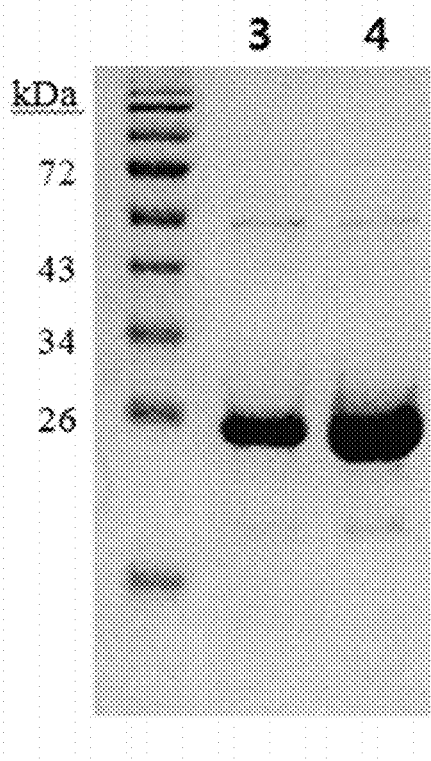
[Fig. 22B]

SEQUENCE LISTING

<160> NUMBER OF SEQ ID NOS: 54

<210> SEQ ID NO 1
<211> LENGTH: 36
<212> TYPE: DNA
<213> ORGANISM: Artificial Sequence
<220> FEATURE:
<223> OTHER INFORMATION: Ramp tag R-DsRed

<400> SEQUENCE: 1
gtctgcgtct gctggcactg gcacaactcc aactcc        36

<210> SEQ ID NO 2
<211> LENGTH: 30
<212> TYPE: DNA
<213> ORGANISM: Artificial Sequence
<220> FEATURE:
<223> OTHER INFORMATION: Ramp tag R-GFP

<400> SEQUENCE: 2
tggatatgga taacgcggac gcggcgctca                                    30

<210> SEQ ID NO 3
<211> LENGTH: 27
<212> TYPE: DNA
<213> ORGANISM: Artificial Sequence
<220> FEATURE:
<223> OTHER INFORMATION: Ramp tag R-BFP

<400> SEQUENCE: 3
gtacgactcc ggctccggca ttgccat                                       27

<210> SEQ ID NO 4
<211> LENGTH: 48
<212> TYPE: DNA
<213> ORGANISM: Artificial Sequence
<220> FEATURE:
<223> OTHER INFORMATION: Ramp tag

<400> SEQUENCE: 4
atggtgcaga ttcagggtca ttacgaactt cagttcgaag cggtacgt                48

<210> SEQ ID NO 5
<211> LENGTH: 24
<212> TYPE: DNA
<213> ORGANISM: Artificial Sequence
<220> FEATURE:
<223> OTHER INFORMATION: Ramp tag R1-BFP

<400> SEQUENCE: 5
catcggcatc gggcacacgc acac                                          24

<210> SEQ ID NO 6
<211> LENGTH: 24
<212> TYPE: DNA
<213> ORGANISM: Artificial Sequence
<220> FEATURE:
<223> OTHER INFORMATION: Ramp tag R2-BFP

<400> SEQUENCE: 6
ggtcccggtc ccaagcctaa gcct                                          24

<210> SEQ ID NO 7
<211> LENGTH: 20
<212> TYPE: DNA
<213> ORGANISM: Artificial Sequence
<220> FEATURE:
<223> OTHER INFORMATION: Primer bfp-RT-F

<400> SEQUENCE: 7
atcgcgttca cctatgtcag                                               20

<210> SEQ ID NO 8
<211> LENGTH: 20
<212> TYPE: DNA
<213> ORGANISM: Artificial Sequence
<220> FEATURE:
<223> OTHER INFORMATION: Primer bfp-RT-R

<400> SEQUENCE: 8
ttcatcgtgc gttcgtagag                                               20

<210> SEQ ID NO 9
<211> LENGTH: 18
<212> TYPE: DNA
<213> ORGANISM: Artificial Sequence

```
<220> FEATURE:
<223> OTHER INFORMATION: Primer gapART-F

<400> SEQUENCE: 9
tgatccggct aacctgaa                                                 18

<210> SEQ ID NO 10
<211> LENGTH: 18
<212> TYPE: DNA
<213> ORGANISM: Artificial Sequence
<220> FEATURE:
<223> OTHER INFORMATION: Primer gapRT-R

<400> SEQUENCE: 10
gcggtgatgt gtttacga                                                 18

<210> SEQ ID NO 11
<211> LENGTH: 18
<212> TYPE: DNA
<213> ORGANISM: Artificial Sequence
<220> FEATURE:
<223> OTHER INFORMATION: Ramp tag R-ClyA

<400> SEQUENCE: 11
ccgctagtat gtgtatgt                                                 18

<210> SEQ ID NO 12
<211> LENGTH: 36
<212> TYPE: DNA
<213> ORGANISM: Artificial Sequence
<220> FEATURE:
<223> OTHER INFORMATION: Ramp tag R-SmGlu

<400> SEQUENCE: 12
gctacagcta cactttcact ttcattgcca ttgcca                             36

<210> SEQ ID NO 13
<211> LENGTH: 18
<212> TYPE: DNA
<213> ORGANISM: Artificial Sequence
<220> FEATURE:
<223> OTHER INFORMATION: Ramp tag R-CAT

<400> SEQUENCE: 13
ctcagactca gacttcta                                                 18

<210> SEQ ID NO 14
<211> LENGTH: 36
<212> TYPE: DNA
<213> ORGANISM: Artificial Sequence
<220> FEATURE:
<223> OTHER INFORMATION: Ramp tag R1-ansB

<400> SEQUENCE: 14 ctcccccctcc ccttgccttt gcctgagcca gagcca                            36

<210> SEQ ID NO 15
<211> LENGTH: 18
<212> TYPE: DNA
<213> ORGANISM: Artificial Sequence
<220> FEATURE:
<223> OTHER INFORMATION: Ramp tag R2-ansB

<400> SEQUENCE: 15
ccatggccat ggtgcgag                                                 18
```

<210> SEQ ID NO 16
<211> LENGTH: 30
<212> TYPE: DNA
<213> ORGANISM: Artificial Sequence
<220> FEATURE:
<223> OTHER INFORMATION: Ramp tag R-1767

<400> SEQUENCE: 16
gctcgagctc gattactatt actagtttgt                                    30

<210> SEQ ID NO 17
<211> LENGTH: 36
<212> TYPE: DNA
<213> ORGANISM: Artificial Sequence
<220> FEATURE:
<223> OTHER INFORMATION: Ramp tag T-BCN

<400> SEQUENCE: 17
gtgtgcgtgt gccagtgtca gtgtgtccgg gtccgg                             36

<210> SEQ ID NO 18
<211> LENGTH: 30
<212> TYPE: DNA
<213> ORGANISM: Artificial Sequence
<220> FEATURE:
<223> OTHER INFORMATION: Ramp tag R-hIL-1beta

<400> SEQUENCE: 18
gctctagctc tatatacata tacatggaga                                    30

<210> SEQ ID NO 19
<211> LENGTH: 24
<212> TYPE: DNA
<213> ORGANISM: Artificial Sequence
<220> FEATURE:
<223> OTHER INFORMATION: Ramp tag R-sIL1beta

<400> SEQUENCE: 19
acgcggacgc ggtggctatg gcta                                          24

<210> SEQ ID NO 20
<211> LENGTH: 24
<212> TYPE: DNA
<213> ORGANISM: Artificial Sequence
<220> FEATURE:
<223> OTHER INFORMATION: Ramp tag R-mIL1beta

<400> SEQUENCE: 20
gctctagctc tattgtgttt gtgt                                          24

<210> SEQ ID NO 21
<211> LENGTH: 36
<212> TYPE: DNA
<213> ORGANISM: Artificial Sequence
<220> FEATURE:
<223> OTHER INFORMATION: Ramp tag R-smIL1beta

<400> SEQUENCE: 21
ctcatactca tacttcccct tcccacgtgc acgtgc                             36

<210> SEQ ID NO 22
<211> LENGTH: 33
<212> TYPE: DNA
<213> ORGANISM: Artificial Sequence
<220> FEATURE:
<223> OTHER INFORMATION: Ramp tag R-IL32beta

```
<400> SEQUENCE: 22 gggatagggga tacttacact tacatactcg tac                                   33

<210> SEQ ID NO 23
<211> LENGTH: 36
<212> TYPE: DNA
<213> ORGANISM: Artificial Sequence
<220> FEATURE:
<223> OTHER INFORMATION: Ramp tag R1-IL32beta

<400> SEQUENCE: 23
gtaatagtaa tacttacact tacatacagg tacagg                                 36

<210> SEQ ID NO 24
<211> LENGTH: 30
<212> TYPE: DNA
<213> ORGANISM: Artificial Sequence
<220> FEATURE:
<223> OTHER INFORMATION: Ramp tag R2-IL32beta

<400> SEQUENCE: 24
gcgaggggca taacctcgct gctaagccga                                        30

<210> SEQ ID NO 25
<211> LENGTH: 33
<212> TYPE: DNA
<213> ORGANISM: Artificial Sequence
<220> FEATURE:
<223> OTHER INFORMATION: Ramp tag R1-IL32beta

<400> SEQUENCE: 25
cttacactta cagggatagg gatatactcg tac                                    33

<210> SEQ ID NO 26
<211> LENGTH: 33
<212> TYPE: DNA
<213> ORGANISM: Artificial Sequence
<220> FEATURE:
<223> OTHER INFORMATION: Ramp tag R2-IL32beta

<400> SEQUENCE: 26
gggtcggggt cgcttacact tacatacata tac                                    33

<210> SEQ ID NO 27
<211> LENGTH: 33
<212> TYPE: DNA
<213> ORGANISM: Artificial Sequence
<220> FEATURE:
<223> OTHER INFORMATION: Ramp tag R3-IL32beta

<400> SEQUENCE: 27
tacatataca tagggacagg gacactttcg ctt                                    33

<210> SEQ ID NO 28
<211> LENGTH: 33
<212> TYPE: DNA
<213> ORGANISM: Artificial Sequence
<220> FEATURE:
<223> OTHER INFORMATION: Ramp tag RY-1767

<400> SEQUENCE: 28
ctacgactac gatcctgttc ctgtgctctc gct                                    33

<210> SEQ ID NO 29
```

<210> SEQ ID NO 29
<211> LENGTH: 36
<212> TYPE: DNA
<213> ORGANISM: Artificial Sequence
<220> FEATURE:
<223> OTHER INFORMATION: Ramp tag RC-b3fv

<400> SEQUENCE: 29
aacttaaact tagtttgtgt ttgtagtcgc agtcgc    36

<210> SEQ ID NO 30
<211> LENGTH: 24
<212> TYPE: DNA
<213> ORGANISM: Artificial Sequence
<220> FEATURE:
<223> OTHER INFORMATION: Ramp tag RM-b3fv

<400> SEQUENCE: 30
ctttgtcttt gtgagcgtga gcgt    24

<210> SEQ ID NO 31
<211> LENGTH: 30
<212> TYPE: DNA
<213> ORGANISM: Artificial Sequence
<220> FEATURE:
<223> OTHER INFORMATION: Ramp tag RH-ansB

<400> SEQUENCE: 31
ccattaccat tatgccgttg ccgtacaacg    30

<210> SEQ ID NO 32
<211> LENGTH: 24
<212> TYPE: DNA
<213> ORGANISM: Artificial Sequence
<220> FEATURE:
<223> OTHER INFORMATION: Ramp tag RP-BCN

<400> SEQUENCE: 32
aggctgaggc tgcagtgcca gtgc    24

<210> SEQ ID NO 33
<211> LENGTH: 24
<212> TYPE: DNA
<213> ORGANISM: Artificial Sequence
<220> FEATURE:
<223> OTHER INFORMATION: Ramp tag RL-CD20

<400> SEQUENCE: 33
tacacgtaca cgaaagcgaa agcg    24

<210> SEQ ID NO 34
<211> LENGTH: 21
<212> TYPE: DNA
<213> ORGANISM: Artificial Sequence
<220> FEATURE:
<223> OTHER INFORMATION: Ramp tag RH-CD20

<400> SEQUENCE: 34
gattgtgatt gtaagcgtaa g    21

<210> SEQ ID NO 35
<211> LENGTH: 21
<212> TYPE: DNA
<213> ORGANISM: Artificial Sequence
<220> FEATURE:
<223> OTHER INFORMATION: Ramp tag RL-alpha

<400> SEQUENCE: 35

```
catgcgcatg cgtacttata c                                          21

<210> SEQ ID NO 36
<211> LENGTH: 24
<212> TYPE: DNA
<213> ORGANISM: Artificial Sequence
<220> FEATURE:
<223> OTHER INFORMATION: Ramp tag RH-alpha

<400> SEQUENCE: 36
aaccgtaacc gtgattgtga ttgt                                       24

<210> SEQ ID NO 37
<211> LENGTH: 27
<212> TYPE: DNA
<213> ORGANISM: Artificial Sequence
<220> FEATURE:
<223> OTHER INFORMATION: Ramp tag RN1-VIM2

<400> SEQUENCE: 37
gactgcgact gccatactca tactgaa                                    27

<210> SEQ ID NO 38
<211> LENGTH: 27
<212> TYPE: DNA
<213> ORGANISM: Artificial Sequence
<220> FEATURE:
<223> OTHER INFORMATION: Ramp tag RN2-VIM2

<400> SEQUENCE: 38
gatcacgatc acgagtcaga gtcacat                                    27

<210> SEQ ID NO 39
<211> LENGTH: 24
<212> TYPE: DNA
<213> ORGANISM: Artificial Sequence
<220> FEATURE:
<223> OTHER INFORMATION: Ramp tag RP1-VIM2

<400> SEQUENCE: 39
aagtgtaagt gtcgccgacg ccga                                       24

<210> SEQ ID NO 40
<211> LENGTH: 27
<212> TYPE: DNA
<213> ORGANISM: Artificial Sequence
<220> FEATURE:
<223> OTHER INFORMATION: Ramp tag RP2-VIM2

<400> SEQUENCE: 40
aaacggaaac ggcatagaca tagacgt                                    27

<210> SEQ ID NO 41
<211> LENGTH: 30
<212> TYPE: DNA
<213> ORGANISM: Artificial Sequence
<220> FEATURE:
<223> OTHER INFORMATION: Ramp tag RH1-BFP

<400> SEQUENCE: 41
ctccacggtc accaatgcta tcactaccac                                 30

<210> SEQ ID NO 42
<211> LENGTH: 36
<212> TYPE: DNA
```

```
<213> ORGANISM: Artificial Sequence
<220> FEATURE:
<223> OTHER INFORMATION: Ramp tag RH2-BFP

<400> SEQUENCE: 42
gtacgggtac acagtcacag tcggcatcga catcga                              36

<210> SEQ ID NO 43
<211> LENGTH: 30
<212> TYPE: DNA
<213> ORGANISM: Artificial Sequence
<220> FEATURE:
<223> OTHER INFORMATION: Ramp tag R1-BCN

<400> SEQUENCE: 43
gtgtgcgtgt gccagtgtca gtgtgtccgg                                     30

<210> SEQ ID NO 44
<211> LENGTH: 24
<212> TYPE: DNA
<213> ORGANISM: Artificial Sequence
<220> FEATURE:
<223> OTHER INFORMATION: Ramp tag R2-BCN

<400> SEQUENCE: 44
gtgtgcgtgt gccagtgtca gtgt                                           24

<210> SEQ ID NO 45
<211> LENGTH: 18
<212> TYPE: DNA
<213> ORGANISM: Artificial Sequence
<220> FEATURE:
<223> OTHER INFORMATION: Ramp tag R3-GCN

<400> SEQUENCE: 45
gtgtgcgtgt gccagtgt                                                  18

<210> SEQ ID NO 46
<211> LENGTH: 6
<212> TYPE: PRT
<213> ORGANISM: Artificial Sequence
<220> FEATURE:
<223> OTHER INFORMATION: Protease cleavage site sequence fused with ramp
      tag of Thrombin

<400> SEQUENCE: 46

Leu Val Pro Arg Gly Ser
1               5

<210> SEQ ID NO 47
<211> LENGTH: 18
<212> TYPE: DNA
<213> ORGANISM: Artificial Sequence
<220> FEATURE:
<223> OTHER INFORMATION: Protease cleavage site sequence fused with ramp
      tag (Thrombin)

<400> SEQUENCE: 47
ctggttccgc gtggatcc                                                  18

<210> SEQ ID NO 48
<211> LENGTH: 5
<212> TYPE: PRT
<213> ORGANISM: Artificial Sequence
<220> FEATURE:
<223> OTHER INFORMATION: Protease cleavage site sequence fused with ramp
      tag (Factor Xa)
```

-continued

<400> SEQUENCE: 48

Ile Glu Gly Arg Gly
1               5

<210> SEQ ID NO 49
<211> LENGTH: 15
<212> TYPE: DNA
<213> ORGANISM: Artificial Sequence
<220> FEATURE:
<223> OTHER INFORMATION: Protease cleavage site sequence fused with ramp
      tag of Thrombin

<400> SEQUENCE: 49
atcgaaggtc gtggg                                                    15

<210> SEQ ID NO 50
<211> LENGTH: 8
<212> TYPE: PRT
<213> ORGANISM: Artificial Sequence
<220> FEATURE:
<223> OTHER INFORMATION: Protease cleavage site sequence fused with ramp
      tag (PreScission Protease)

<400> SEQUENCE: 50

Leu Glu Val Leu Phe Gln Gly Pro
1               5

<210> SEQ ID NO 51
<211> LENGTH: 24
<212> TYPE: DNA
<213> ORGANISM: Artificial Sequence
<220> FEATURE:
<223> OTHER INFORMATION: Protease cleavage site sequence fused with ramp
      tag (PreScission Protease)

<400> SEQUENCE: 51
ctggaagttc tgttccaggg gccc                                          24

<210> SEQ ID NO 52
<211> LENGTH: 30
<212> TYPE: RNA
<213> ORGANISM: Artificial Sequence
<220> FEATURE:
<223> OTHER INFORMATION: Hypothetical m-RNA sequence for explaining the
      determination of frequency of usage of codons

<400> SEQUENCE: 52
auggccaccu accccgacac cgccgacugu                                    30

<210> SEQ ID NO 53
<211> LENGTH: 564
<212> TYPE: DNA
<213> ORGANISM: Artificial Sequence
<220> FEATURE:
<223> OTHER INFORMATION: synthetic sequence of recombinant protein

<400> SEQUENCE: 53
atgtgcttcc cgaaggtcct ctctgatgac atgaagaagc tgaaggcccg aatgcaccag     60
gccatagaaa gattttatga taaaatgcaa aatgcagaat caggacgtgg acaggtgatg    120
tcgagcctgg cagagctgga ggacgacttc aaagagggct acctggagac agtggcggct    180
tattatgagg agcagcaccc agagctcact cctctacttg aaaaagaaag agatggatta    240
cggtgccgag gcaacagatc ccctgtcccg gatgttgagg atcccgcaac cgaggagcct    300

```
gggagagct tttgtgacaa ggtcatgaga tggttccagg ccatgctgca gcggctgcag    360
acctggtggc acggggttct ggcctgggtg aaggagaagg tggtggccct ggtccatgca    420
gtgcaggccc tctggaaaca gttccagagt ttctgctgct ctctgtcaga gctcttcatg    480
tcctctttcc agtcctacgg agcccacgg ggggacaagg aggagctgac accccagaag    540
tgctctgaac cccaatcctc aaaa                                           564

<210> SEQ ID NO 54
<211> LENGTH: 36
<212> TYPE: DNA
<213> ORGANISM: Artificial Sequence
<220> FEATURE:
<223> OTHER INFORMATION: Ramp tag sequence

<400> SEQUENCE: 54
gggataggga tacttacact tacatactcg tactcg                              36
```

UNIVERSAL PROTEIN OVEREXPRESSION TAG COMPRISING RAMP FUNCTION, AND APPLICATION THEREOF

CROSS REFERENCE TO RELATED APPLICATIONS

This application is a National Stage of International Application No. PCT/KR2014/001616, filed on Feb. 27, 2014, which claims priority from Korean Patent Application No. 10-2013-0027549, filed on Mar. 14, 2013, the contents of all of which are incorporated herein by reference in their entirety.

TECHNICAL FIELD

The present invention relates to a synthetic tag capable of improving difficult-to expression/non-expression problem of a recombinant protein in a cell. More specifically, the tag behaves (controls translation speed by recruiting of tRNA and providing re-use of tRNA) both in inside/outside of a target gene in transcription or translation steps, such that translation speed inhibition and non-uniform protein expression problems caused when there is a rare codon of a host in a hybrid gene may be solved to stably induce functional over-expression of the protein.

BACKGROUND ART

A useful protein may be generally divided into proteins for pharmaceuticals and related research such as immunomodulators, enzyme inhibitors, and hormones, or industrial proteins such as proteins for diagnosis and adding enzymes for biotransformation. A process for mass-producing these proteins necessarily requires gene expression, culture, and purification technologies. In particular, the expression technology occupies the most important part in the process for protein production, and is a key indicator for judging economic feasibility, and accordingly, the technology is a main process for increasing value-added or utility. In the related art, a method of screening bacterial host or animal cell line having high productivity, producing a desired protein from the cell line, and separating and purifying the desired protein has been used to obtain a specific protein. However, this method has problems in that an obtained amount is limited, and at the time of being applied to other proteins, the same productivity may not be guaranteed, and it is difficult to obtain products with homogenous qualities (the same protein in view of a structure and function). Recently, in accordance with development of recombinant DNA (genetic engineering) technology, a method in which a large amount of desired protein is easily obtained by transforming the useful gene into *E. coli*, plant cell line, or animal cell line, has been commonly used. In particular, since productivity is linked with cost, mass-production of recombinant protein using microorganisms (single cells such as *E. coli*, yeast, *actinomyces*) having an advantage of being rapidly cultured with high concentration in relatively cheap medium is known to have a significantly great advantage in view of commercial aspect. In addition, these hosts are well-defined in view of physiological/genetic characteristics, and effective methods and techniques for recombinant gene manipulation are well developed. Accordingly, due to an advantage in which desired useful protein is obtainable with high efficiency, medicinal proteins including insulin and industrial enzyme, and the like, have been produced successfully. It is known that animal/plant hosts having relatively complex physiological/genetic traits and regulatory mechanism require a difficult genetic manipulation/regulation process, such that utilization frequency thereof is relatively low in expressing a foreign gene besides a pharmaceutical protein with the purpose of application to a living body. However, at the time of universally utilizing expression regulatory mechanism, the above-described disadvantage is possible to be overcome, such that a lot of researches into discovery and improvement of an expression control method capable of being applicable equally to all eukaryotic cell lines including also prokaryotic cell lines have been conducted.

Expression systems for recombinant protein production have attempt engineering access in vectors, hosts, and ORF level, and prototypes of related and developed technique are relatively well known (Marino, M. H., Biopharm. 2 (1989) 18-33; Goeddel, D. V. et al., Methods Enzymol. 185 (1990) 3-7; Wurm, F. and Bernard, A., Curr. Opin. Biotechnol. 10 (1999) 156-159). Successful expression of a number of foreign genes has been reported by various strategies and technical modifications based on these prototype techniques; however, due to lack of generalization logic, a process of re-optimization for a portion or all of the components of an expression system depending on specific genes, has been generally required. In this process, a strategy of inducing an increase in an amount of transcript by combination of a strong promoter and regulatory elements, and a secondary structure of the transcript, and an expression strategy focusing on an increase of thermodynamic stability of the transcript are used. However, it is known that this strategy lacks generalization with the applicability to all proteins, and more fundamentally, there remains a problem in that cases where there is no significant correlation between the transcript and an amount of translated protein frequently occur. Recently, as a solution to this problem, a new strategy related with an increase in efficiency of protein translation or translational rate control is known as a potential logic that is possible to achieve generalization.

Low expression efficiency occurring in the translation step is caused by coding sequences (codon) of foreign genes having codon usage frequency showing different patterns from protein coding sequences of an innate gene which is well expressed in host cells. It is known that since codon preference in tRNA pool of a host coevoluted by making a pair of codon in a genome coding region is significantly biased, each amino acid is translated with biased codon for each cell. In addition, it is well known that bias in the process of using the codon is capable of changing peptide elongation rate (Sørensen M. A. et al., 1993). Accordingly, the most effective production for recombinant proteins needs to change and control foreign gene codon in consideration of codon usage of a host, as well as improvement at a transcription module level in consideration of vector sequence (promoter and operator) and factors interacting the vector sequence that are considered to increase transcription efficiency. As one of the various methods for solving the protein translation inhibition problem, a codon optimization technique was developed. As an attempt to increase the translation speed of a protein encoding region which is inefficient in the translation, the codon optimization technique generally uses a strategy for replacing codons (rare codons) that are rarely used or infrequently used in host cells with preferred codons.

Codon optimization is to increase translation speed by decreasing rare codon ratio in a wild type foreign gene. According to the codon optimization, an expression amount of recombinant protein is increased, which is easily achieved using a computer on the basis of a host-specific codon usage table. When the sequence of a target gene is input and the codon table of the host used in the expression is input, substitution with the codon showing a relative high frequency is made to obtain results in order of score. However, since DNA in which wild-type ORF base sequences of DNA are changed into other sequences encoding the same type of amino acids (synonymous codon) needs to be artificially synthesized, cost may be increased. In addition, various kinds of genes need to be synthesized and tested according to a codon sorting/classification method, and cases in which an improved amount of expression is not exhibited as compared to the wild-type gene, unlike expectations, are frequently observed. More extremely, it has been reported that an expression amount is more increased in codon de-optimization (strategy of changing preferred codons to rare codons by applying a logic opposite to optimization) rather than codon optimization. A method of supplementing an amount of tRNA for corresponding codon (rare codon) has also been attempted as circuitous solution of recombinant protein expression efficiency due to a difference in codon usage (Lee, Su Jeong et al., 2006). In this process, a method of additionally adding a plasmid into a host cell, the plasmid encoding specific tRNA that is insufficient in host cells has been attempted. However, this method has also a disadvantage in that it is required to provide a vector including a target gene together with the plasmid encoding the specific tRNA. In addition, intracellular stability and difficulty in obtaining a reproducible result that are fundamental problems of dual vector-expression system still remain as a challenge to be solved.

The present invention provides a universal protein over-expression tag including a ramp function as a novel method capable of increasing translation efficiency. When the ramp tag is used to increase translation efficiency, it is not necessary to change original ORF sequence, which is unlike codon optimization, such that there is no change in protein intrinsic activity, and DNA artificial synthesis according to codon substitution is not required, which is also economical in view of cost. In addition, the tag is capable of securing functional fusion with other sequences as much as possible, and is capable of guaranteeing grafting supremacy to be grafted with other functional tags. Accordingly, a technology of designing a tag capable of rapidly increasing translation efficiency at low cost has an important economic/industrial effect. In particular, it is expected that this universal expression theory (use only tag) will remarkably increase production yield of foreign protein in animal/plant cell lines that has relatively complicated regulatory mechanisms and thus has some limitations for general use.

DISCLOSURE

Technical Problem

An object of the present invention is to provide an over-expression method of a recombinant protein in a novel scheme capable of reducing cost consumed for gene synthesis, being rapidly performed, and being variously utilized by developing a tag consisting of 1 to 20 codons having ramp function capable of controlling a translation speed and fusing the tag with the inside/outside of a target gene, unlike the existing codon optimization requiring change of a lot of base sequences of gene through the entire region.

Another object of the present invention is to provide selection criteria of a rare codon configuring the tag in an organism of which a codon table is established and an arrangement of the codon.

Another object of the present invention is to provide a method of producing and providing a universal ramp tag capable of being applied to various recombinant proteins, and a method of applying the universal ramp tag to an expression cassette.

Another object of the present invention is to provide a method of controlling gene expression capable of being utilized by using a method of producing a tag suitable for the host and the recombinant protein.

Technical Solution

In one general aspect, the present invention provides a method of scheme of collecting rare codons in each host cell, a method of configuring a tag including a ramp function with respect to a target gene, and an operation principle of the tag to increase translation efficiency.

Accordingly, the present invention provides a method of producing a ramp tag for controlling translation speed, including: making a rare codon table according to a host cell; converting DNA sequence of a target gene into codons; analyzing frequency and position at which rare codons in the rare codon table appear in an open reading frame (ORF) of the target gene; and collecting and arranging the rare codons having an appearance frequency of 3 times or less. Preferably, the collecting of the rare codons may be performed by analyzing gene in which frequency of the codons is 0.5 to 3%, and the number of isoacceptor tRNA genes is 0 to 2 to thereby produce the ramp tag. The rare codons may be arranged by considering frequency and position at which rare codons appear in the ORF. Preferably, the frequency in which the rare codons appear in the open reading frame (ORF) may be 0.5 to 2%, and the position thereof may be in order of the first half. The host cell may be selected from the group consisting of prokaryotic cells (bacteria or archaea) and eukaryotic cells (yeast, fungi, insect, plant, animal, human). Preferably, the host cell may be selected from the group consisting of *E. coli*, yeast, a Chinese hamster ovary cell (CHO cell line), a human cell (*Homo sapiens* cell line), a plant cell (*Arabidopsis thaliana*), and the like. More preferably, the host cell may be selected from the group consisting of *E. coli* K-12, *saccharomyces cerevisiae*, CHO-K1, HEK293t, and the like. The ramp tag may consist of 1 to 20 codons. Preferably, the ramp tag may consist of 1 to codons including a preferred codon between the rare codons. More preferably, the ramp tag may consist of 1 to codons including a preferred codon in which the frequency appearing in the ORF is 0.5 to 2% between the rare codons. In the case of producing a tag with the multi-purposes, the multi-purpose ramp tag capable of inducing over-expression of protein and performing pure separation may be produced by arranging rare codons of generally used His-tag in the tag. In addition, the target gene may be a gene encoding a high-value commercial or difficult to express protein, preferably, the gene may encode esterase, β-glucosidase, cytolysin A, chloramphenicol acetyltransferase (CAT), neopullulanase, interleukin-1, interleukin-32, recombinant antibody (single chain Fv: scFv), asparaginase B, tetra-cell adhesion molecule (T-CAM), B3(Fv)PE38, anti-B-lymphocyte antigen CD20 (anti-CD20), or anti-tumor necrosis factor alpha (anti-TNFα).

Further, the present invention provides a ramp tag for controlling translation speed, produced by the preparation method according to the present invention. Preferably, the ramp tag may be selected from the group consisting of SEQ ID NOS: 1 to 42.

In addition, the present invention provides a method of increasing an expression efficiency of a difficult to expression protein in a host cell, including: collecting rare codons in the host cell; configuring a ramp tag with respect to a target gene; producing an expression vector including the ramp tag and the target gene; transforming the host cell with an expression vector; culturing a transformed host cell in a culture medium that is suitable for expressing the protein; and inducing over-expression and purification by using a histidine rare codon, thereby increasing expression/purification efficiency of protein. The collecting of the rare codons may be performed by analyzing copy number of tRNA corresponding rare codon in which frequency of the codons is 0.5 to 2%, and the number of isoacceptor tRNA genes is 0 to 2. The rare codons of the ramp tag may be arranged by considering frequency and position at which rare codons appear in a target gene. Preferably, the frequency at which the rare codons appear in the open reading frame (ORF) may be 0.5 to 2%, and the position thereof may be in order of the first half. In addition, the codon order of the ramp tag may be combined and arranged.

The host cell may be selected from the group consisting of prokaryotic cells (bacteria or archaea) and eukaryotic cells (yeast, fungi, insect, plant, animal, human). Preferably, the host cell may be selected from the group consisting of *E. coli*, yeast, a Chinese hamster ovary cell (CHO cell line), a human cell (*Homo sapiens* cell line), a plant cell (*Arabidopsis thaliana*), and the like. More preferably, the host cell may be selected from the group consisting of *E. coli* K-12, *saccharomyces cerevisiae*, CHO-K1, HEK293t, and the like. The ramp tag may consist of 1 to 20 codons. Preferably, a preferred codon may be included between the rare codons. More preferably, the preferred codon in which the frequency appearing in the ORF is 0.5 to 2% may be included between the rare codons. In addition, the target gene may be a gene encoding a high value commercial protein or difficult to expression protein, preferably, the gene may encode esterase, β-glucosidase, cytolysin A (ClyA), recombinant antibody (single chain Fv: scFv), asparaginase B, tetra-cell adhesion molecule (T-CAM), B3(Fv)PE38, chloramphenicol acetyltransferase (CAT), neopullulanase, interleukin-1, interleukin-32, anti-B-lymphocyte antigen CD20 (anti-CD20), or anti-tumor necrosis factor alpha (anti-TNFα). The ramp tag may be positioned so as to be fused to 5' or 3' of the target gene, or be introduced into an inner portion of the target gene, or be independently translated. The ramp tag may be additionally used together with other tags or fusion proteins, and the other tag may be at least one selected from the group consisting of His tag, T7 tag, S-tag, Flag-tag, HA-tag, V5 epitope, PelB, and Xpress epitope tag. The fusion protein may be selected from the group consisting of GST, MBP, NusA, CBP, GFP, Thioredoxin, Mistic, Sumo and DSB. In addition, the ramp tag may have a specific cleavage site at fused 5'- or 3'-terminal region of target protein or polypeptide. The selected cleavage site (signal sequence) may also be recognized and treated by host cell machinery (for example; cleavage by signal peptidase). The signal sequence may be selected from the recognition sequences by protease groups consisting of lgA-protease, granzyme B, Tev protease, prescission protease, thrombin, a factor Xa, alkaline phosphatase, penicillinase, lpp, enterokinase, and heat-stable enterotoxin II leaders.

The ramp tag may be applied with the expression system for increasing expression of recombinant protein. In general, an element of protein expression plasmid is a structural unit of plasmid including at least one expression cassette for expressing prokaryote replication origin, prokaryote selection marker, eukaryote selection marker, and target gene expression module (each gene includes transcription termination factor including a promoter, a ribosome recognition site, 5'-UTR, structural gene and 3'-UTR signal). Replication origin derived from plasmid pBR3222 is suitable for most of gram-negative bacteria, 2μ plasmid origin is suitable for yeast, and various viral origins (SV40, polyoma, adenovirus, VSV or BPV) are useful for an expression vector in mammalian cells. The expression vector may generally contain a promoter recognized by an innate host system, and the promoter suitable for being used in a prokaryotic host may be an araBAD promoter, a phoA promoter, and a hybrid promoter such as a beta-lactamase and lactose promoter system, alkaline phosphatase, tryptophan (trp) promoter system, and a tac promoter, and the like. However, other known bacteria promoters (gram-positive promoter or promoter with broad spectrum range) may also be appropriate. In addition, for optimized translation, Shine Dalgarno Sequence, or RBS preceding a start codon of mRNA or its variants may also be included in 5'-untranslated region. Promoter sequences of eukaryotic cells are well known. The promoter sequences suitable for being used in yeast host may include promoters for glycolytic enzymes such as 3-phosphoglycerate kinase or enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triosephosphate isomerase, phosphoglucose isomerase and glucokinase. Other yeast promoters having an inducible promoter having additional benefits of control by growth conditions may include promoter parts for alcohol dehydrogenase 2, isocytochrome C, acid phosphatase, and may include promoter parts for a degradative enzyme related with nitrogen metabolism, enzymes involved in using metallothionein, glyceraldehyde-3-phosphatedehydrogenase, and maltose and galactose. Vectors and promoters that are suitable for being used for yeast expression are disclosed in EP No. 73,657. In addition, yeast enhancers are advantageously used with the yeast promoters.

Transcription from vectors in mammalian host cells is controlled by promoters obtained from genome of polyoma virus, fowlpox virus, adeno virus 2, bovine papilloma virus, avian sarcoma virus, cytomegalo virus, retro virus, hepatitis-B virus, and most preferably, simian virus 40 (SV40), and promoters obtained from hybrid mammalian promoters (actin promoter, immunoglobulin promoter, and the like), and heat-shock promoter, wherein these promoters are compatible with the host cell system. For optimized translation, Kozak sequence may be included in a 5' untranslated region. In addition, the expression vector used in eukaryotic host cells (yeast, fungi, insect, plant, animal, human cells) may include sequences required for transcription termination and mRNA stability. In the case of mRNA processing procedure, in particular, mRNA splicing and processing, polyadenylation and processing signal as well as mRNA splicing signal may be included according to the characteristics (exon/intron ratio, length, etc.) of a structural gene.

The present invention provides a strategy to fuse a ramp tag for improving translation speed consisting of codon sequences shown in FIG. 2 with a target gene to be functioned and a strategy of independently expressing the ramp tag.

It may be observed that even though the ramp tag according to the present invention is positioned so as to be fused to 5' or 3' of the target gene, or be introduced into an inner portion of the target gene, or be independently translated, an expression efficiency of the target protein may be increased, and a total protein amount may be increased by about 2.5 to 7.5 times as compared to a control group.

The present invention provides a method of producing a customized ramp tag in a fluorescent protein gene known as a reporter protein, and measuring an increase in an expression amount of protein to prove model establishment of the tag.

The present invention provides a method of producing a customized ramp tag in a gene that is known to have difficulty in expression (that is, a difficult to expression gene) by using the expression tag and measuring an increase in an expression amount of gene to prove functionality of the tag.

The present invention intermittently arranges a histidine rare codon for the purpose of purification in the ramp tag to thereby produce a ramp tag capable of inducing over-expression and performing easy separation of a target protein with a single process, and the present invention includes proving functionality of this tag.

In the present invention, when producing customized ramp tags aimed at industrial enzymes having high value but difficulty in expression and protein drugs such as esterase, β-glucosidase, cytolysin A, chloramphenicol acetyltransferase, neopullulanase, asparaginase B, and measuring an expression amount of these proteins by using *E. coli* and eukaryotic cells as a host, clear expression and an increase in activity may be confirmed as compared to a control group.

When producing customized ramp tags aimed at cytokine having high value for medical and research and hormones (interleukin-1 and interleukin-32) and measuring expression amounts of these proteins by using *E. coli* and eukaryotic cells as a host, noticeable increase in protein amount and increase in activity as compared to a control group may be confirmed.

When producing customized ramp tags aimed at recombinant antibody (single chain Fv, scFv), tetra-cell adhesion molecule (T-CAM), B3(Fv)PE38, anti-B-lymphocyte antigen CD20 (anti-CD20), anti-tumor necrosis factor alpha (anti-TNFα) used as useful proteins for diagnosis or treatment, and measuring expression amounts of these proteins by using eukaryotic cells as a host, noticeable increase in expression level as compared to a control group may be confirmed.

In addition, the present invention provides a method of using a ramp tag, including: fusing the ramp tag as described above with commercialized other tags or fusion partner.

Even in a case in which the ramp tag according to the present invention is used with fusion proteins with other tags such as His-tag, T7-tag, and HA-tag, or fusion proteins such as GST, GFP, MBP, and the like, it may be confirmed that an expression amount of desired protein may be increased without interfering with functions thereof.

In addition, the present invention provides a method of intermittently grafting the ramp tag as described above with a rare codon that is bindable to affinity chromatography to thereby induce over-expression and easy separation of a target protein.

When an applicable histidine rare codon is intermittently grafted at the time of producing the ramp tag according to the present invention, it may be confirmed that an expression amount of desired protein may be increased, and it may be confirmed that pure separation of the target protein may be performed by a single purification process.

In addition, the present invention provides a method of removing a ramp tag from a protein which is expressed by fusing the ramp tag according to the present invention with a signal sequence or the ramp tag as described above with a specific cleavage site. The protein cleavage site may be present on sequences recognized by IgA-protease, granzyme B, Tev protease, prescission protease, thrombin, a factor Xa, or enterokinase, but is not limited thereto.

Even in a case in which the ramp tag is used together with the signal sequence or the specific cleavage site in order to separate the ramp tag according to the present invention and the target protein, it may be confirmed that an expression amount of desired protein may be increased without interfering with functions thereof, and even after the ramp tag is removed, it may be confirmed that there is no change in activity or stability of the target protein.

Further, the present invention provides a method of applying and using the ramp tag according to the present invention with the existing expression system known in the art.

Even in a case in which the ramp tag according to the present invention is used together with an inducible promoter, Kozak sequence, mRNA splicing signal, polyadenylation signal, or shine-dalgarno-sequence, it may be confirmed that an expression amount of the target protein may be more increased even without interfering with functions of the target protein, as compared to a case in which the expression system is used alone.

In addition, the present invention provides a method of applying an appropriate codon length of the ramp tag.

When a length of the sequence of the ramp tag is decreased and used for the target protein according to the present invention, an increase in an expression amount of the target protein may be confirmed, and when a length of the sequence of the ramp tag is increased, an increase in an expression amount of the target protein may be confirmed.

Further, the present invention provides a method of combining and arranging codon order of the ramp tag.

When the codon order of the ramp tag according to the present invention is changed, it may be confirmed that there is no significant difference between an expression amount of the above case and an expression amount of the target protein increased by the existing ramp tag.

Further, the present invention provides a method of expressing a multiple gene in a vector.

Even in the case in which target genes applied by the ramp tag according to the present invention are expressed in one vector, it may be confirmed that each amount of protein may be increased as compared to the control group, and even in the case in which the target genes are applied to other vectors, it may be confirmed that expression amounts of the target proteins may be increased.

Further, the ramp tag according to the present invention may be used for over-expression of a target gene in eukaryotes as well as prokaryotes.

Even in the case in which the ramp tag according to the present invention is expressed in a microorganism and the eukaryote in addition to *E. coli*, it may be confirmed that an expression amount of the target protein may be increased.

Further, the present invention provides a method of using a ramp tag to increase solubility of a target protein.

When the ramp tag according to the present invention is used for the target protein, expression of protein and an increase in solubility may be confirmed.

Further, the present invention provides a method of using a ramp tag to increase stability of a target protein.

When the ramp tag according to the present invention is used for the target protein, both the expression of protein and an increase in stability may be confirmed.

Further, the present invention provides a method of using a ramp tag to increase enzymic activity of a target protein.

When the ramp tag according to the present invention is used for the target protein, both the expression of protein and an increase in enzymic activity may be confirmed.

Advantageous Effects

The present invention provides a novel method capable of increasing translation efficiency in a method of producing a recombinant protein by analyzing and collecting a rare codon and producing a ramp tag. Unlike the codon optimization or codon de-optimization method, the novel method according to the present invention may increase translation efficiency even though original ORF sequence is not changed.

Accordingly, since a gene level of DNA artificial synthesis for substituting codon is not required, cost may be reduced, codon length and arrangement sequence of the ramp tag may be organically controlled depending on an object, and universal ramp tag is possible to be designed, thereby rapidly increasing translation efficiency on various proteins. In addition, at the time of arranging the rare codon that is bindable to affinity chromatography in the tag, there is provided a method of simultaneously performing over-expression and pure separation.

According to the present invention, even though the ramp tag with respect to the target protein is incorporated at various positions (introduction into N-terminal, C-terminal, or the inside of gene), and the ramp tag is positioned so as to be translated into an independent peptide, an expression amount of the target protein may be increased, even though the ramp tag is used together with various tags or fusion proteins, an expression amount of the target protein may be increased while maintaining functions of the tags or the fusion proteins.

In addition, when the ramp tag is used together with a plasmid level of expression system for over-expression of the target protein, an expression amount of the target protein may be more increased even without interfering with functions of the target protein as compared to a case in which the expression system is used alone. The above-described effect may solve a codon usage compatibility problem of foreign genes and host cells to control an amount of protein, such that a difficult to expression problem of a target protein when yeast, animal cells, plant cells as well as E. coli are host may be solved.

According to the method of the present invention, the ramp tag may be designed to be customized according to drug proteins such as ClyA, scFV, asparaginase B(ansB), T-CAM, and B3(Fv)PE38 to be directly usable for mass-production of pharmaceuticals or industrial enzymes. Further, when the ramp tag is removed from a protein expressed by fusing the ramp tag according to the present invention with a signal sequence or specific cleavage site, the intact target protein may be obtained to confirm structure and activity of the original protein.

In addition, solubility of the target protein may be increased, formation of non-active inclusion body may be inhibited, and the like, to remove necessity of a refolding process of an insoluble protein, such that economic feasibility may be significant during a scale-up production for industrial production. Further, enzymic activity and stability of the protein may be continuously maintained to obtain the target product at a high yield, such that active protein required for biotechnology and pharmaceuticals may be supplied in mass-production.

DESCRIPTION OF DRAWINGS

FIG. 1A and FIG. 1B are a diagram showing an effect (A) of a rare codon in a translation process and a principle (B) showing solution using a ramp tag, respectively. In FIG. 1A, the sequence AUG GCC ACC UAC CCC GAC ACC GCC GAC UGU (SEQ ID NO: 52) is a hypothetical m-RNA sequence used to explain the determination of the frequency of the usage of codons according to an embodiment. In FIG. 1B, the sequence of CUA CCC UGU shows codons at positions 1-9 of SEQ ID NO: 52, and the sequence of AUG GCC ACC UAC CCC GAC ACC GCC shows codons at positions 10-30 of SEQ ID NO: 52.

FIG. 2A and FIG. 2B are a diagram showing strategy of function (A) and expression (B) by fusing a ramp tag for improving a translation speed with a target gene, respectively. In FIG. 2A, the sequence (SEQ ID NO: 53) in a box shows codons of a recombinant protein, and the Ramp tag sequence (SEQ ID NO: 54) is obtained by according to an embodiment.

FIG. 3A, FIG. 3B and FIG. 3C show analysis of expression amounts of fluorescent proteins DsRed(A), GFPuv(B), and mBFP(C) including the ramp tag of the present invention, respectively, using SDS-PAGE. In FIGS. 3A-3C, R represents proteins fused with the tag (Lane NC, pTrc99A; T, total protein; S, soluble protein).

FIG. 4 shows analysis of expression amounts of fluorescent protein mBFP including introduction of ribosome binding site (RBS) and the ramp tag of the present invention, using SDS-PAGE. In FIG. 4, R represents proteins fused with the tag (Lane 1, pTrc99A; 2, pTrc99A-mBFP; 3, RBS-introduced pTrc99A-mBFP; 4, pTrc99A-R1-mBFP; 5, RBS-introduced pTrc99A-R1-mBFP; 6, RBS-introduced pTrc99A-R2-mBFP).

FIG. 5 shows analysis of amounts of transcript (mRNA) of fluorescent protein mBFP including the ramp tag of the present invention, using RT-PCR (Bar 1, pTrc99A-mBFP; 2, RBS-introduced pTrc99A-mBFP; 3, pTrc99A-R1-mBFP; 4, RBS-introduced pTrc99A-R1-mBFP; 5, RBS-introduced pTrc99A-R2-mBFP).

FIG. 6 is a growth curve showing analysis of physiological effects of E. coli host transformed with fluorescent protein mBFP including the ramp tag of the present invention. In FIG. 6, R represents proteins fused with the tag (Symbol A, pTrc99A; Symbol B, pTrc99A-mBFP; Symbol C, pTrc99A-R-mBFP).

FIG. 7 shows analysis of expression amounts of esterase (1767) and neopullulanase (BCN) including the ramp tag of the present invention. In FIG. 7, R represents proteins fused with the tag (T, total protein; S, soluble protein).

FIG. 8A and FIG. 8B show analysis of an expression amount (A) and an enzymic activity (B) of chloramphenicol acetyltransferase (CAT) including the ramp tag of the present invention, respectively. The enzymic activity was measured by MIC measurement, and R represents proteins fused with the tag (T, total protein; S, soluble protein; w/o, without IPTG; w/, with IPTG).

FIG. 9A and FIG. 9B show analysis of an expression amount (A) and an enzymic activity (B) of asparaginase B (ansB) including the ramp tag of the present invention, respectively. The enzymic activity was measured by zymogram measurement (Lane 1, pBAD; lane 2, pBAD-R1-ansB; lane 3, pBAD-R2-ansB; lane 4, pBAD-ansB).

FIG. 10 shows results obtained by confirming in vivo stability of asparaginase B (ansB) including the ramp tag of the present invention, depending on time. R represents proteins fused with the tag, and stability was confirmed by inducing protein expression in samples and measuring stability of the samples as time passes, using western blot.

FIG. 11 shows SDS-PAGE analysis results showing an expression amount measured by fusing the ramp tag of the present invention at C-terminal of chloramphenicol acetyl-transferase (CAT). R represents proteins fused with the tag, and an indication by R is a position indicating the tag fused at a terminal of CAT.

FIG. 12A and FIG. 12B show analysis of expression amounts of human-derived interleukin-1 (A) and mouse-derived interleukin-1 (B) including the ramp tag of the present invention, respectively. R represents proteins fused with the tag, and h is a human-derived gene, m is a mouse-derived gene, and s is codon-optimized synthetic gene (T, total protein; S, soluble protein; I, IPTG-induced expression of protein).

FIG. 13A and FIG. 13B show analysis of expression amounts of total protein (A) and a soluble protein (B) of interleukin-32 including the ramp tag of the present invention, respectively. R represents proteins fused with the tag, and expression amounts were confirmed using western blot (Lane 1, pTrc99A-IL32β; 2, pTrc99A-R-IL32β; 3, pTrc99A-IL32γ; 4, pTrc99A-R1-IL32γ; 5, pTrc99A-R2-IL32γ).

FIG. 14 shows analysis of an expression amount of interleukin-32 by combining rare codon order of the ramp tag of the present invention. R represents proteins fused with the tag, and expression amounts were confirmed using western blot (Lane 1, pTrc99A-IL3213; 2, pTrc99A-R-IL32β; 3, pTrc99A-R1-IL3213; 4, pTrc99A-R2-IL32p; 5, pTrc99A-R3-IL32β).

FIG. 15 shows analysis of an expression amount of cytolysin A (ClyA) including the ramp tag of the present invention and a cleavage site sequence. R represents proteins fused with the tag, and the expression amounts were confirmed using western blot (Lane 1, pET; 2, pET-ClyA; 3, pET-R1-ClyA; 4, pET-R2-ClyA; 5, pET-R3-ClyA; 6, pET-R1-ClyA; 7, pET-R2-ClyA; 8, pET-R3-ClyA; w/o, without Protease; w/, with Protease).

FIG. 16A and FIG. 16B show analysis of an expression amount (A) of 1-deoxy-D-xylulose-5-phosphate synthetase (dxs) and IPP isomerase (idi) including the ramp tag of the present invention and also shows a lycopene production amount (B) by E. coli strain transformed with this construct, respectively. R represents proteins fused with the tag, and the production amounts were confirmed using HPLC (Lane 1, pTrc99A; 2, pTrc99A-dxs-idi; 3, pTrc99A-R-dxs-R-idi; WT, pTrc99A-dxs-idi; RT, pTrc99A-R-dxs-R-idi).

FIG. 17 shows analysis of expression amounts of esterase (1767) including the ramp tag of the present invention. R represents proteins fused with the tag, and the expression amounts were confirmed using western blot (1767, pYES2-1767; RY-1767, pYES2-RY-1767; T, total protein; S, soluble protein; I, insoluble protein).

FIG. 18 shows analysis of an expression amount of B3(Fv)PE38 gene including the ramp tag of the present invention in a Chinese hamster ovary cell (CHO cell). R represents proteins fused with the tag, and s is codon-optimized synthetic gene. The expression amounts were confirmed using western blot (Lane 1, pCMV; 2, pCMV-B3Fv; 3, pCMV-sB3Fv, 4, pCMV-RC-B3Fv).

FIG. 19 shows analysis of an expression amount of B3(Fv)PE38 gene including the ramp tag of the present invention in a mouse embryo fibroblast (NIH 3T3 cell). R represents proteins fused with the tag, and s is codon-optimized synthetic gene. The expression amounts were confirmed using western blot (Lane 1, pCMV; 2, pCMV-B3Fv; 3, pCMV-sMB3Fv, 4, pCMV-RM-B3Fv).

FIG. 20 shows analysis of an expression amount of asparaginase B (ansB) including the ramp tag of the present invention in a human cell (HEK 293t cell). R represents proteins fused with the tag, and the expression amounts were confirmed using western blot (ansB, pCMV-ansB; RH-ansB, pCMV-RH-ansB; T, total protein; S, soluble protein; I, expression-induced protein).

FIG. 21A, FIG. 21B, and FIG. 21C show analysis of antibiotic susceptibility test of clones harboring beta-lactamase VIM2 including the ramp tag of the present invention in LB medium (A) and M9 mediums (B, C) (w/o, without $Zn^{2+}$; w/, with $Zn^{2+}$).

FIG. 22A shows analysis of protein (mBFP) expression amounts increased by ramp tag including histidine rare codon, thereby simultaneously having protein expression and purification function in the ramp tag of the present invention, and FIG. 22B shows the purity (B) of purifying proteins by separation using affinity chromatography (Lane 1, pTrc99A; 2, pTrc99A-mBFP; 3, pTrc99A-RH1-mBFP; 4, pTrc99A-RH2-mBFP).

BEST MODE

Hereinafter, the present invention will be described in more detail by the following Examples. However, the present invention is not limited to the following examples, and it will be apparent to those skilled in the art that various modification and changes may be made without departing from the scopes and spirits of the present invention.

Here, unless technical and scientific terms used herein are defined otherwise, they have meanings understood by those skilled in the art to which the present invention pertains. In addition, repeated descriptions for technical constitution and function as the same as the related art will be omitted.

The present invention constitutes a method for collecting rare codons in each host. The rare codon described herein refers to codons collected in a process to be explained below in addition to a concept of the generally known rare codon. When a codon is decoded, a translation speed is the most significantly affected depending on how quickly aa-tRNA having a state in which amino acids are bound is supplied. Accordingly, the translation speed is rapid in the codons in which an amount of corresponding aa-tRNA is sufficient in a cell, and conversely, a translation efficiency is deteriorated by lack of aa-tRNA. Accordingly, gene copy of tRNA may be used as a first measure that is possible to infer a concentration of the corresponding tRNA in the cell. As known in the art, a typical codon optimization reflects codon frequency, which is because it is known that codon frequency is proportional to corresponding tRNA copy number. Table 1 below shows codon frequency (on the basis of 100%) and tRNA gene copy for each amino acid (AA) in E. coli K-12 (http://gtrnadb.ucsc.edu/).

TABLE 1

Constitution of codon usage of E. coli K-12 strain

| AA | Codon | Frequency | tRNA |
|---|---|---|---|
| < 2 Box tRNA Sets > ||||
| F | Phe | UUU | 2.22 | |
| | | UUC | 1.65 | 2 |
| H | Asn | AAU | 1.77 | |
| | | AAC | 2.16 | 4 |
| K | Lys | AAG | 1.03 | |
| | | AAA | 3.37 | 5 |

TABLE 1-continued

Constitution of codon usage of E. coli K-12 strain

|   | AA | Codon | Frequency | tRNA |
|---|---|---|---|---|
| D | Asp | GAU | 3.22 | |
|   |   | GAC | 1.91 | 3 |
| E | Glu | GAG | 1.78 | |
|   |   | GAA | 2.94 | 4 |
| H | His | CAU | 1.29 | |
|   |   | CAC | 0.97 | 1 |
| Q | Gln | CAG | 2.89 | 2 |
|   |   | CAA | 1.54 | 2 |
| C | Cys | UGU | 0.50 | |
|   |   | UGC | 0.64 | 1 |
| Y | Tyr | UAU | 1.60 | |
|   |   | UAC | 1.22 | 3 |

< 4 Box tRNA Sets >

| A | Ala | GCU | 1.53 | |
|---|---|---|---|---|
|   |   | GCC | 2.56 | 2 |
|   |   | GCG | 3.37 | |
|   |   | GCA | 2.02 | 3 |
| G | Gly | GGU | 2.48 | |
|   |   | GGC | 2.97 | 4 |
|   |   | GGG | 1.11 | 1 |
|   |   | GGA | 0.79 | 1 |
| P | Pro | CCU | 0.70 | |
|   |   | CCC | 0.55 | 1 |
|   |   | CCG | 2.32 | 1 |
|   |   | CCA | 0.34 | |
| T | Thr | ACU | 0.39 | |
|   |   | ACC | 2.34 | 2 |
|   |   | ACG | 1.44 | 2 |
|   |   | ACA | 0.70 | 1 |
| V | Val | GUU | 1.83 | |
|   |   | GUC | 2.53 | 2 |
|   |   | GUG | 2.62 | |
|   |   | GUA | 1.09 | 5 |

< 6 Box tRNA Sets >

| S | Ser | UCU | 0.30 | |
|---|---|---|---|---|
|   |   | UCC | 0.28 | 2 |
|   |   | UCG | 0.83 | 1 |
|   |   | UCA | 0.72 | 1 |
|   |   | AGU | 0.87 | |
|   |   | AGC | 2.80 | 1 |
| A | Arg | CGU | 2.09 | 4 |
|   |   | CGC | 2.20 | |
|   |   | CGG | 0.54 | 2 |
|   |   | CGA | 0.33 | |
|   |   | AGG | 0.22 | 2 |
|   |   | AGA | 0.20 | 2 |
| L | Leu | CUU | 1.10 | |
|   |   | CUC | 1.11 | 1 |
|   |   | CUG | 3.29 | 4 |
|   |   | CUA | 0.39 | 3 |
|   |   | UUG | 2.30 | 2 |
|   |   | UUA | 2.39 | 2 |

< 3 Box tRNA Sets >

| I | Ile | AUU | 3.04 | |
|---|---|---|---|---|
|   |   | AUC | 2.32 | 2 |
|   |   | AUA | 0.43 | |

TABLE 1-continued

Constitution of codon usage of E. coli K-12 strain

|   | AA | Codon | Frequency | tRNA |
|---|---|---|---|---|
| W | Trp | UGG | 1.53 | 1 |
| M | Met | AUG | 2.78 | 8 |
|   | Stop | UAA | 0.22 | |
|   |   | UAG | 0.03 | |
|   |   | UGA | 0.09 | 1 |

It may be appreciated that when considering the codon frequency of Table 1 above, there are a number of amino acids that are not proportional to tRNA genes. In addition, it may be appreciated that even though the codon frequency is high, tRNA gene is not present, which may be explained because anti-codon of tRNA recognizes other codons due to a wobble phenomenon (non-Watson-Crick complementary binding at third position) (Table 2). The tRNA capable of reading two or more codons refers to an isoacceptor tRNA. For example, tRNA (anti-codon GAA) that reads UUC of phenylalanine also reads UUU. In E. coli K-12, tRNA having anti-codons G and U decodes most of U, C, A, G codons.

TABLE 2

Decodable codons by wobble phenomenon of anti-codons

| 5' Base in anticodon | 3' Base in codon |
|---|---|
| G | U or C |
| C | G |
| A | U |
| U | A or G |
| I | A, U or C |

When selecting the rare codon in consideration of lack of tRNA, it is required to select a codon capable of reusing tRNA in the ORF in consideration of isoacceptor tRNA. For example, a UCU codon showing low frequency among codons capable of encoding serine in the ORF is possible to inhibit a translation speed; however, when the UCC appears in front of the UCU codon, tRNA used in UCC is capable of being re-used to decode UCU, such that the UCU does not inhibit translation speed. Accordingly, codon frequency is calculated by adding up two codon frequencies read by the isoacceptor tRNA to be calculated as one in the following analysis process. The codon frequency of phenylalanine is 3.87% which is the sum of two codons thereof, and in the case of Ser, the total of three codon frequencies are 1.66%, 1.60%, and 2.47% obtained by dividing codons into two codons as shown in Table 1, and the number of tRNA gene copies corresponding thereto are also regarded as 2, 2, 1, obtained by adding up two codons. As one characteristic of the codon usage, codon bias is strongly shown in amino acids having three or more synonymous codons (Table 1). For example, glycine shows frequencies of 5.45% and 1.90% to have a gap between numbers. Similar to this, arginine shows codon frequencies of 4.29%, 0.89%, and 0.31% to have large gap. Meanwhile, it may be appreciated that amino acids encoded with two codons in E. coli, such as tyrosine, histidine, glutamine, aspartate, lysine, asparagine, are decoded into one isoacceptor tRNA, thereby having only one kind of tRNA gene, and in most of them, both of the codons exhibit high frequency of about 2-5%, which has weak codon bias.

[Example 1] New Definitions and Collection Criteria of Rare Codons in E. coli

Two or more isoacceptor tRNAs are involved in translation of amino acid: serine, leucine, valine, proline, threonine, alanine, arginine, glycine encoded with three or more codons (expressed by 3, 4, and 6 box, respectively, according to the number of codons), and there are abundant cases in which codon pairs (isoacceptor tRNAs is regarded as one) which are considered two or more, such that it is possible for the gap between frequencies to be high. It may be appreciated that when a number of codons are not present in the ORF, codon rarity is large in 3-6 box in which tRNA is difficult to be sufficiently secured. Accordingly, it may be appreciated that a strategy of securing sufficient translation efficiency by re-using tRNA is necessarily needed in 3-6 box codon in which the isoacceptor tRNA is insufficient. In order to obtain the effect, the strategy of the present invention consists of collecting codon sequence with low utilization frequency to configure a tag, positioning the tag in front of a target gene for expression, and previously collecting and re-using rare codon tRNAs inducing serious problems in expression efficiency of gene (FIG. 1). The re-use of the tRNAs recruited by the configured tag is an object, and accordingly, a decrease in concentration of amino acid in vivo according to an increase in frequency of tRNA use by the tag is not considered in the present invention.

Next, there are provided conditions of collecting the rare codons in consideration of the codon usage. As a complement to the existing conventional method, a method of considering each codon frequency and a method of considering gene copy number of the isoacceptor tRNA were mixed. The conditions of collecting the rare codons on the basis of the codon frequency were as follows: 1. The frequency of codon pairs in each amino acid is 1.0% or less (these threshold values correspond to levels in which 34.4% (21 codons) of the total number of codons is collectable); 2. Maximally three codons for one amino acid are only collected.

Cut-off values of the above-described conditions need to consider how the total codons of E. coli are distributed, and therefore, distribution with the axis of the codon frequencies and the number of tRNA gene is referred (Table 3).

TABLE 3

Distribution of codon frequencies and the number of tRNA genes

| * | 0~0.5 | 0.5~1 | 1~1.5 | 1.5~2 | 2~3 | 3(%)~ | Total |
|---|---|---|---|---|---|---|---|
| *** | 1 | 0 | 1 | 1 | 1 | 1 | 5 |
| 0 | 2 | 4 | 2 | 4 | 3 | 2 | 17 |
| 1~2 | 3 | 10 | 5 | 5 | 4 | 0 | 27 |
| 3~4 | 0 | 1 | 1 | 1 | 4 | 2 | 9 |
| 5~8 | 0 | 0 | 1 | 0 | 1 | 1 | 3 |
| Total | 6 | 15 | 10 | 11 | 18 | 6 | 61 |

* tRNA,
** Codon frequency,
*** efficient wobble

Most of codons encoding amino acids exhibit distribution of 0 to 2 tRNA genes and 0.5 to 3% or more of codon frequency. Here, in order to collect the rare codons, the criterion such as the above-described parenthesis was applied, and the test results include 9 codons determined as the rare codons. In this way, a scheme of simultaneously considering the codon frequency and the isoacceptor tRNA was selected. Table 4 shows finally collected rare codons of E. coli K-12 strain.

TABLE 4

Collected rare codons of E. coli K-12 strain

| AA | | Codon | Frequency | tRNA |
|---|---|---|---|---|
| < 2 Box tRNA Sets > | | | | |
| H | His | CAC | 0.97 | 1 |
| C | Cys | UGU | 0.50 | |
| | | UGC | 0.64 | 1 |
| < 4 Box tRNA Sets > | | | | |
| G | Gly | GGA | 0.79 | 1 |
| P | Pro | CCU | 0.70 | |
| | | CCC | 0.55 | 1 |
| | | CCA | 0.84 | 1 |
| T | Thr | ACU | 0.89 | |
| | | ACA | 0.70 | 1 |
| < 6 Box tRNA Sets > | | | | |
| S | Ser | UCU | 0.80 | |
| | | UCC | 0.86 | 2 |
| | | UCA | 0.71 | 1 |
| R | Arg | CGA | 0.35 | |
| | | AGG | 0.11 | 1 |
| | | AGA | 0.20 | 1 |
| L | Len | CUA | 0.39 | 1 |
| < 3 Box tRNA Sets > | | | | |
| I | Ile | AUA | 0.43 | |

On the basis of the above-description, the present invention provides a method of configuring a ramp tag and explains a principle showing functions thereof. The ramp tag is an arrangement consisting of about 1 to 20 codons. The configuration and arrangement may vary depending on gene to be fused with the ramp tag. In addition, a length of the ramp tag may consist of 20 or more codons depending on a length of a target gene or the degree of rare codon distribution in the gene. However, at the time of using a transcriptional coupling technique, there is a possibility that amino acids are insufficient due to tags to be expressed separately from the target gene (the ratio of the amino acids used for tag expression is increased), such that the length of the tag is required to be limited.

[Example 2] Configuration of Sequences and Construct of Ramp Tag to be Fused with Each Gene Referring to FIG. 2A, the ramp tag is configured by the following process: 1. Making rare codon table and preferred codon table depending on host; 2. Converting DNA sequences of target gene into codons; 3. Analyzing frequency and position at which codons in the codon table as made above appear in an open reading frame (ORF) of the target gene; 4. Combining analyzed codons and arranging the codons in the ramp tag; 5. Inducing expression by fusing or substituting the tag at N- or C-terminal inner and outer part (1 to 20 codons corresponding to the tag length) of the target gene.

According to the configuration of the tag, tRNA required in ORF translation is primarily used when ribosome decodes the tag, and then re-usable in the ORF. FIG. 1B illustrates the translation process and explains operation principle and strategy of the ramp tag. In order to properly operate the ramp tag, the ramp tag needs to be recharged with amino acids by aminoacyl-tRNA synthase before the tRNA used for protein translation is re-used in ribosome. Accordingly, as the operating condition of the present invention, once used tRNA is not spread out while the translation process is in progress, but recharged with the amino acid, in order to be easily re-used.

The codon arrangement of the tag considers the frequency and position at which the codons appear in the ORF. In order to provide a re-using effect of the tRNA by the ramp tag more deeply in the translation process, among the rare codons, codons that have little appearance frequency in ORF but delay the translation process, and that have a distribution position near to N-terminal or that appear periodically in the ORF are selected. That is, among the rare codons, the rare codons are analyzed in the order in which appearance frequency of the rare codons is decreased in the ORF, and then cases in which the analyzed codons are positioned in the first half in the ORF are primarily arranged. It is known that when the only rare codons are combined to be used at the time of configuring the ramp tag, the translation process is inhibited, and it results in a decrease in yield of protein production. That is, it has been reported that when only two rare codons are continuously arranged in ORF of *E. coli*, translation is partially inhibited (She P. et al., 2006). Therefore, in order to solve the translation problem of the continuously arranged rare codon by combination of the rare codon and preferred codon, the preferred codons are classified and combined by the analysis method described above. The combinations among the codons may have the preferred codons positioned between the rare codons, but the number of preferred codons, a primarily arranged order in the ramp tag, and repeatability of the same codon may vary depending on target proteins.

In order to provide the codon of the ramp tag for protein over-expression (or for expression of difficult to expressed protein) in the present invention, the possibility of model establishment with a fusion form in which the tag is fused with the target gene at inner and outer parts was confirmed. Customized tags and gene structures fused with the tag aimed at fluorescent proteins DsReD, GFP, and mBFP were designed. Referring to FIG. 2B, the tag is fused so as to be positioned to the outside of N-terminal (or 5' terminal) of a gene or is expressed in an independent form. However, the present invention is not limited thereto, and the ramp sequence may be designed to be incorporated into the inside of N-terminal of the gene by replacing high frequency codon by rare codon using primer so that amino acids of wild-type protein are not changed, to thereby be simply introduced by PCR. In the next example, DNA sequences of the tags for each gene were shown. First, customized tags were fused with the above-described three genes to attempt over-expressions in expression vectors (with inducible promoter), resulting a phenomenon in which tRNA is insufficient. As another test control group, a vector capable of expressing the target gene without any inducer (hereinafter, referred to as a constitutive expression vector) was used.

[Example 3] Analysis of Expression Amount by Ramp Tag Fusion in Fluorescent Proteins DsReD, GFP, and mBFP The following Table 5 shows lists of codon sequences of the ramp tag for each gene. The ramp tags consisting of rare codons were prepared by the process of FIG. 2, and were located at N-terminal region to fuse with the target gene, thereby functioned for inducing expression. Over-expression effects of the ramp tag were confirmed by using the constitutive expression vectors such as pBEM3, pRCEMT and an inducible expression vector such as pET22b(+). After the gene is primarily cloned into each vector, the tag sequences of Table 5 (gene-specific ramp tag sequence) were synthesized with a start codon ATG, followed by PCR using each gene as a template, to obtain a gene fragment fused with the ramp tag. Then, a restriction enzyme recognition site of a multi-cloning site was cleaved and cloned, and transformed into *E. coli* XL1-blue and BL21. The recombinant gene may stably maintain a vector having fluorescent protein, and may be used in any known *E. coli* cells capable of measuring fluorescence. For example, *E. coli* JM109 or RR1, LE392 or W3110, or the like, and yeast such as *Saccharomyces, Phichia*, or the like, which is an eukaryotic cell may also be used as hosts when subcloned the gene with a ramp tag into *E. coli*-yeast shuttle vector.

When the host cell is a prokaryotic cell, a method of carrying the vector having the gene with a ramp tag of the present invention into the host cell may be performed by a $CaCl_2$ method, a FSB solution treatment, an electric shock method, and the like. In addition, when the host cell is an eukaryotic cell, the vector having the recombinant gene may be injected into the host cell by an electric shock method, a liposome-mediated transfection, and the like.

The transformed single colony was inoculated in 5 ml liquid medium (LB+50 mg/ml ampicillin), and pre-cultured under conditions of 37° C. and 200 rpm for 12 hours. When an absorbance ($OD_{600}$) of the culture reached 2.0, the culture was inoculated in 200 ml of liquid medium (LB+50 mg/ml ampicillin), and cultured under the same conditions, and then when the absorbance ($OD_{600}$) value was 0.5, expression through Ptac promoter was induced by 0.1 mM isopropyl-β-D-1-thiogalactopyranoside (IPTG). After 3 hours, the culture was subjected to sampling, and cell density was measured by absorbance ($OD_{600}$) values. Subsequently, cell density was controlled to satisfy $OD_{600}$=2.0, and 1 ml of aliquots were centrifuged at 7,000 rpm for 5 minutes. Then, the supernatant was removed and a protein expression amount was analyzed by SDS-PAGE using the resulting pellet (cell precipitate).

TABLE 5

Gene-specific ramp tag sequence

| Gene | Gene with tag | Ramp tag sequence |
|---|---|---|
| DsRed | R-DsRed | GTCTGCGTCTGCTGGCACTGGCACA ACTCCAACTCC (Sequence 1) |
| GFPuv | R-GFP | TGGATATGGATAACGCGGACGCGGC GCTCA (Sequence 2) |

TABLE 5-continued

Gene-specific ramp tag sequence

| Gene | Gene with tag | Ramp tag sequence |
|---|---|---|
| mBFP | R-BFP | GTACGACTCCGGCTCCGGCATTGCC AT (Sequence 3) |

As a result, it was observed that when comparing the inducible expression vector with IPTG added thereto and the control group in view of protein expression amount, using SDS-PAGE, total protein amount was increased 3.7 to 5.8 times or more in DsRed (R-DsRed) fused with the tag (FIG. 3A). It shows an increase in protein expression amount by recruiting tRNA and then providing re-use function from the fusion with the tag. Similar to this, as a result obtained by analyzing an effect of the ramp tag on GFPuv and mBFP, it could be confirmed that total protein amounts of GFPuv(R-GFP) and mBFP(R-BFP) fused with the ramp tag were increased 5.4 times, and 2.6 times or more, respectively, as compared to control groups (GFPuv and BFP) (FIGS. 3B and 3C). When the culturing was performed under the same condition without adding an inducer (IPTG), an expression amount obtained therefrom was similar to that of a case in which over-expression was induced by an inducer, or was increased 3.5 to 7.8 times or more when compared to those of the proteins expressed without ramp tag.

[Example 4] Analysis of Expression Amount by Existing Expression Elements and Ramp Tag Fusion The present Example provides a method of using the ramp tag together with typical recombinant protein expression-enhancing elements. An inducible promoter was used as a component of the existing *E. coli* expression plasmid, and a ribosome binding site (RBS) was introduced in front of an initiation codon of the mRNA for optimized translation. In addition, optimized elements of a transcript secondary structure were included in 5' untranslated region (UTR). In the case of a mammalian cell, mammalian replication origin (SV40 origin) was included as a component of plasmid, and an inducible promoter was used. For optimized translation, Kozak sequence was included in 5' untranslated region. The ramp tag was fused by including elements in which a possibility of forming mRNA secondary structure is reduced and splicing signals to analyze expression of the protein. As a result, an increase in an expression amount due to the ramp tag without interfering with the expression system performing special functions in inducing stability or effective transcription/translation could be confirmed in a prokaryotic host (*E. coli*) (FIG. 4). Functional evaluation was conducted by mounting an inducible promoter Ptrc, a ribosome binding site, and forced transcription termination sites (transcription terminator signals T1 and T2) on the plasmid, and fusing the ramp tag with the fluorescent protein mBFP. The used ramp tags were shown in Table 6.

Even in a test of fusing ramp tag with the gene coding for the target protein expressed in an eukaryotic host with the existing expression element, the same effect was verified, and accordingly, it was confirmed that the ramp tag was capable of being easily grafted with the existing system.

TABLE 6

Gene-specific ramp tag sequence

| Gene | Gene fused with tag | Ramp tag sequence |
|---|---|---|
| BFP | R1-BFP | CATCGGCATCGGGCACACG CACAC (Sequence 5) |
| | R2-BFP | GGTCCCGGTCCCAAGCCTA AGCCT (Sequence 6) |

[Example 5] Measurement of mRNA Level by Ramp Tag Sequence in Transcription Step It was confirmed through the above-described Examples that the ramp tag sequences increase an expression amount of protein. Accordingly, in order to confirm whether the increase in expression amounts of the proteins due to a difference in ramp tag sequence affects an amount of transcript (mRNA) transcribed from each DNA as well as a translation step, a gene expression level at the transcription step and the translation step of the fluorescent protein mBFP were analyzed. After the vectors were prepared by the same method as Example 3 above and expressed, the protein expression amount was analyzed in the translation step by SDS-PAGE electrophoresis. Then, in order to confirm an amount of mBFP transcript of the prepared sample, RT-PCR was performed. First, total RNA was extracted from *E. coli* cells transformed with the vectors, using a Trizol reagent (Invitrogen, Cat no. 15596-026) method. In a reverse transcription reaction using the extracted RNA as a template, cDNA was synthesized by using the separated RNA (0.2 μg) and Superscript™ II reverse transcriptase (Invitrogen, Cat. No. 18064-022). Then, polymerase chain reaction (PCR) was carried out in ExTaq (TaKaRa, Cat No. RR001A). As a control, GAPDH gene was used. Primers used for confirmation of the transcript amounts of mBFP were indicated in Table 7 below, and PCR conditions were carried out at an annealing temperature fixed to 55° C. As a result, it could be confirmed that the transcript amount of R1-BFP and R2-BFP obtained by introducing RBS was about 1.7 to 2.4 times higher than that of the control group without the tag (FIG. 5).

Accordingly, the present inventors found through the above-described results that the difference in protein expression amount by the ramp tag provides an incidental effect of increasing stability and/or expression level of transcript (mRNA) to increase the protein expression amount as well as a major effect of increasing expression by recruiting tRNA and providing a re-use function in the translation step. In addition, it is also assumed that the above results are obtained because a translational rate of the ribosome bound to the transcript is well controlled by the ramp tag, a ratio of transcript exposed to endonuclease is relatively small, and recycling of ribosome is effectively induced.

TABLE 7

RT-PCR primer sequence

| Name of primer | Sequence |
|---|---|
| BFP-RT-F | ATCGCGTTCACCTATGTCAG (Sequence 7) |
| BFP-RT-R | TTCATCGTGCGTTCGTAGAG (Sequence 8) |

TABLE 7-continued

RT-PCR primer sequence

| Name of primer | Sequence |
|---|---|
| gapART-F | TGATCCGGCTAACCTGAA (Sequence 9) |
| gapRT-R | GCGGTGATGTGTTTACGA (Sequence 10) |

[Example 6] Analysis of Effect on Host Growth Having Ramp Tag Fusion Gene

In order to confirm whether the ramp tag triggers stress on host growth in the present Example, cell growth curve of a host (*E. coli*) having a fluorescent protein mBFP fused with the tag and expression level of stress proteins obtained therefrom were analyzed. After the vectors were prepared by the same method as Example 3 above, transformed hosts were cultured, and cells of which expression was induced with 0.1 mM isopropyl-thio-β-D-1-thiogalactopyranoside (IPTG) were subjected to sampling according to time, and cell concentration was measured by absorbance values at $OD_{600}$. The same samples were further subjected to SDS-PAGE electrophoresis to measure protein expression amount. As a result, as shown in FIG. 6, it may be confirmed that there is no growth difference between the strain having the ramp tag fused gene and the control group, and after the induction of protein expression, the increase in protein amount could be clearly confirmed as compared to the control group. There are also no distinct expressions of stress proteins induced by the overexpression of foreign gene. Accordingly, it may be appreciated through the above-described results that the ramp tag induces over-expression of protein without inducing stress on the cell growth of the strain.

[Example 7] Effect of Ramp Tag on the Expression of Difficult to Express Protein for Industrial or Medical Use The above-described effect of the ramp tag was applied to economically valuable difficult to express proteins for industrial and medical application. The drug proteins such as cytolysin A (ClyA) and asparaginase B (AnsB), and the industrial enzymes such as esterase (1767), β-glucosidase (SmGlu), neopullulanase (BCN), chloramphenicol acetyl-transferase (CAT) have significantly broad application range, but have difficulty in mass-production. When these proteins were used to express with the ramp tags as described below and subjected to the analyses of expression amounts by the same method as Example 3, an increase in protein amount (2.1-4.8 times) could be clearly confirmed as compared to the control group (FIG. 7). In order to confirm whether the over-expressed protein is functionally active, enzymatic activities of chloramphenicol acetyl transferase (CAT) and asparaginase B (AnsB) were measured by using a disc diffusion assay and zymography, respectively. The disc diffusion assay was performed as follows. *E. coli* cells were cultured in a solid medium, and a single colony was inoculated in 10 ml liquid medium, followed by subculture three times. $5×10^5$ cells/ml of the cultured strain were inoculated in 1% agar medium by pour plate method, and then 10 μl of chloramphenicol (30 μg/ml) was dropped to 6 mm paper disc, dried for 5 minutes at room temperature, and positioned in the center of the plate and cultured. After culturing, a size of a growth inhibition zone around the paper disc was measured. As a result, it was confirmed that the functional protein proportional to the corresponding band on SDS-PAGE was over-expressed (FIG. 8).

Whether asparaginase B, a well-known cancer treatment drug, was functionally overexpressed was measured by using activity assay. To this end, an indicator dye was used for measuring pH change (color change) caused by aspartic acid which is a hydrolytic product of a substrate, asparaginase. Zymography for the above measurement is a method of detecting active band with a substrate solution layer (overlaid agar). Briefly, culture broth was centrifuged to be divided into a cell portion (pellet) and supernatant, followed by sonification for cell lysis, and the resulting lysate was subjected to non-denaturing PAGE analysis. The substrate solution layer for detecting activity was prepared by adding 0.1% phenol red to 0.2 M tris-phosphate, 40 mM L-asparagine, 10 mM sodium tetraphenylborate, 1% agar, and activity staining was performed at 37° C. for 2 hours. As a result, it was confirmed that functional protein proportional to the corresponding band on SDS-PAGE was over-expressed (FIG. 9). Accordingly, it was confirmed that the ramp tag induced over-expression of the protein without interfering the enzymic activity. These results were re-verified through comparison test by western blot using the antibody raised against to asparaginase B. Ramp tag sequences used in induction of protein expression in the present Example were shown in Table 8 below.

TABLE 8

Ramp tag sequences for industrial and medical protein gene expression

| Gene | Gene with tag | Ramp tag sequence |
|---|---|---|
| ClyA | R-ClyA | CCGCTAGTATGTGTATGT (Sequence 11) |
| SmGlu | R-SmGlu | GCTACAGCTACACTTTCA CTTTCATTGCCATTGCCA (Sequence 12) |
| CAT | R-CAT | CTCAGACTCAGACTTCTA (Sequence 13) |
| ansB | R1-ansB | CTCCCCCTCCCCTTGCCT TTGCCTGAGCCAGAGCCA (Sequence 14) |
|  | R2-ansB | CCATGGCCATGGTGCGAG (Sequence 15) |
| 1767 | R-1767 | GCTCGAGCTCGATTACTA TTACTAGTTTGT (Sequence 16) |
| BCN | R-BCN | GTGTGCGTGTGCCAGTGT CAGTGTGTCCGGGTCCGG (Sequence 17) |

The above-described results showed that the customized ramp tags designed according to target genes are directly used for production of a pharmaceutical or industrial enzyme guaranteeing functionality.

[Example 8] Analysis of Stability of Recombinant Protein Fused with Ramp Tag

In the present Example, protein stability by the ramp tag and functions of the tag having stability increasing effect incidentally were evaluated. In the case of a drug or enzyme protein, the protein stability provides the promising property in which the proteins are more stably maintained in a living body to double the effect. As known in the art, since signal sequence linked closely with structure, function, and stability may be present at N-terminal region of protein, the ramp tag fused with the target gene at N-terminal regions was tested to provide a protective function or stability of the resulting fusion protein. Target proteins used herein was asparaginase B which is an anti-cancer drug protein, and when the ramp tag used in Example 7 was positioned at N-terminal to induce sufficient protein expression, and 10 µg/ml of cycloheximide was added into the medium to block further expression of a new protein in-vivo, and existence time of the pre-expressed protein in-vivo was confirmed. Examples of inhibitors of protein biosynthesis include chloramphenicol, tetracycline antibiotics (Tetramycin, aureomycin), macrolide-based antibiotics (Erythromycin, Leukomycin), aminoglycoside-based antibiotics (Streptomycin, Kanamycin, Gentamycin, Neomycin, Amikacin), and lincosamide-based antibiotics (Lincomycin, Clindamycin), and the like, but the present invention is not limited thereto. As a result, it was confirmed that the recombinant protein having the ramp tag was maintained in-vivo for a longer time as compared to the control group (FIG. 10). As a result, it may be appreciated that the ramp tag provides an additional function for maintaining of protein over a long time in-vivo while improving expression of the target protein. This property results from an effect in which binding of the chaperone for protein folding is more easily achieved to be protected from protease due to the slow rate of translation at initiation stage of translation by ramp tag, together with an effect in which the unique structure related with half-life of the protein is changed by the ramp tag to avoid regulatory mechanism.

[Example 9] Ramp Tag Effect when Fused at C-Terminal of the Target Protein

Ramp tags in all Examples above were positioned at N-terminal of the target protein. In the translation process of most organisms including eukaryotic cells, the close proximity between 5' and 3'-UTR region of mRNA is observed so that ribosome which decodes mRNA once easily decodes the mRNA again, wherein this phenomenon refers to recycling of ribosome. Accordingly, it is expected that even though the ramp tag is positioned at a C-terminal (or 3' UTR region of transcript) even though it is not translated, an effect that tRNA is re-used may be provided by recycling of ribosome. Based on the above-description, whether or not protein amount is increased was confirmed by fusing the ramp tag to C-terminal region of the target protein or by using translational coupling. The target protein used herein was chloramphenicol acetyltransferase (CAT), and the effect was verified by positioning (CAT-R) the ramp tag used in Example 7 at C-terminal of the target gene. As a result, the expression amounts were increased 4.7-6.5 times or more as compared to the control group which was not fused with the tag. Therefore, it was confirmed that the ramp tag had the protein over-expression inducing ability at C-terminal which is the same as at N-terminal (FIG. 11).

[Example 10] Effect of Ramp Tag Positioned Inside of Gene

In the present Example, a method of introducing the function of the ramp tag by codon substitution of the inside region of the target gene at N-terminal to obtain an overexpression effect was designed and tested. The ramp tags described in the preceding Examples are positioned at the front or the back of the target gene to induce re-use of tRNA. However, it was expected that the re-use of tRNA has the same effect even with a method of substituting the N- or C-terminal codons in the target gene with rare codons without requiring a separate aid of the tag. In particular, it was expected that when the rare codons are collected in the middle or the end part of the gene ORF, at the time of substituting codons that appear in front part with codons that designate the same amino acid as the codons that appear at the middle or end part but are rare, a phenomenon effect that is decreased translation due to spread out of tRNA since it is far from the ramp tag fused at N-terminal could be complemented. On the basis of this assumption, synonymous codon that appears at N-terminal region was substituted with rare codon that appears at middle or C-terminal region of the target gene. For example, in the case of esterase 1767, it may be seen that the synonymous codon (indicated by underlines) of the rare codon of the gene next to the start codon ATG appears intermittently. When the codons ATT, GGT, CTT, CGT are substituted with ATA, GGA, CTA, CGA, respectively, they may function as a ramp tag by itself without change in amino acid.

For example

```
                                    (SEQ ID NO: 4)
ATG GTG CAG ATT CAG GGT CAT TAC GAA CTT CAG
TTC GAA GCG GTA CGT
```

As a test result, it was analyzed that the function of the tag has an effect by a method of positioning the ramp tag at the N- or C-terminal region of the inside of the ORF, and further, the function of the ramp tag has an effect even though 8 to 12 sequences at the N- and C-terminal region of the inside of the gene are substituted (high frequency codon to rare codon) with synonymous codon shown in the middle or the end part of the gene. As a quantitative result through comparison in view of activity using SDS-PAGE, it was confirmed that expression amounts were increased about 2.8-4.7 times.

[Example 11] Effect of Ramp Tag on Cytokine or Hormone Protein

In the present Example, functionality of the ramp tag was applied to difficult to express cytokine protein with high value-added. The cytokine proteins, interleukin-1 and interleukin-32 are immune reactions and cancer treatment candidates, which have significantly broad applicability; however, are not well expressed, or even though expression is induced, inclusion body is formed, such that it is difficult to mass-produce protein in which functionality is guaranteed. The inclusion body (IB) refers to an insoluble protein aggregate caused by aggregation phenomenon of foreign protein expressed in the host cell, which is formed when correct folding of proteins is not generated. The IB induces reduction in enzymic activity and stress in cell growth, such that decreasing the formation of IBs to increase a ratio of soluble proteins is an important indicator for actual production of recombinant protein. In the present Example, the ramp tag was applied to cytokine protein having low expression yield and solubility to confirm an effect. Analyses of an expression amount of a target band which is difficult to be detected due to a low expression yield as compared to relatively general over-expression protein were verified by western blot. The ramp tag sequences used for inducing expression of these proteins were shown in Table 9 below. For Interleukin-1 gene, a human-derived gene (hIL-1β) and a mouse-derived gene (mIL1β) were used, and codon-optimized synthetic genes (sIL1β and smIL1β, commercially synthesized) to which the existing protein over-expression logic was applied, were used as control groups. For Interleukin-32 gene, two ramp tags were designed since rare codons are largely present.

TABLE 9

Ramp tag sequences for cytokine protein gene expression

| Gene | Gene with tag | Ramp tag sequence |
|---|---|---|
| hIL-1β | R-hIL-1β | GCTCTAGCTCTATATAC ATATACATGGAGA (Sequence 18) |
| sIL1β | R-sIL1β | ACGCGGACGCGGTGGCT ATGGCTA (Sequence 19) |
| mIL1 | R-mIL1β | GCTCTAGCTCTATTGTG TTTGTGT (Sequence 20) |
| smIL1β | R-smIL1β | CTCATACTCATACTTCC CCTTCCCACGTGCACGT GC (Sequence 21) |
| IL32β | R-IL32β | GGGATAGGGATACTTAC ACTTACATACTCGTAC (Sequence 22) |
| IL32γ | R1-IL32γ | GTAATAGTAATACTTAC ACTTACATACAGGTACA GG (Sequence 23) |
|  | R2-IL32γ | GCGAGGGGCATAACCTC GCTGCTAAGCCGA (Sequence 24) |

As a result, when comparing protein expression amount of Interleukin-1 with that of control group, by SDS-PAGE, it was observed that total protein amounts were increased 3.7-6.7 times or more in IL-1(R-hIL-1p, R-sIL1β, R-mIL1β, R-smIL1β) fused with the tag (FIG. 12). As shown in FIG. 12, expression was not detected in the codon-optimized genes to which the existing protein over-expression logic was applied. As a result obtained by analyzing an expression yield of interleukin-32 to which the ramp tag was applied, by western blot, it was confirmed that as compared to the control groups, total protein amounts of IL-32(R-IL32β, R1-IL32γ, R2-IL32γ) fused with the ramp tag were increased 2.4-5.5 times or more, and soluble protein amounts thereof were increased 2.3-3.8 times or more (FIG. 13). In addition, protein over-expression was confirmed in both of the ramp tags applied to one target gene, such that the present invention provides various kinds of the ramp tag with respect to the target protein, and accordingly, it shows that ramp tag sequences may be combined in various order for use.

As shown in the above results, for the functional expansion into a universal tag having broad range of application for various genes due to over-expression logic have a advantages over conventional methods, it is require to control position or length of the tag sequence, and in order to obtain a more effective result, it was considered to require translational coupling, that is, independent translation without fusing the tag with the gene in one transcript. Accordingly, the following translational coupling was attempted by inserting stop codon or stop codon and RBS between the ramp tag and the gene.

[Example 12] Functionality Analysis of Tag in which Translational Coupling was Performed In order to translate only the tag into independent peptide rather than the fusion form with the ramp tag and the target protein, a stop codon and RBS were linked to the terminal of the ramp tag using a specific primer. Here, when a length between the ramp tag and the target gene is made only by 1 to 2 base(s), independent translation may be induced without introduction of the RBS. Structures shown in FIG. 2 were produced and expression amounts were analyzed in inducible expression vectors. Target proteins used herein were difficult to express esterase (1767) and β-glucosidase (SmGlu), and effects were verified by using the ramp tag used in Example 7. As a result, it was confirmed that in the case of 1767, even though translational coupling was induced, the protein amount was distinctly maintained, similar to the results shown in FIG. 7. However, for SmGlu, protein expression amount was relatively decreased, such that the effect is obvious, thus the independent expression strategy of the tag for inducing a more consistent result still needs to be improved. This problem is concerned with a problem that efficiency in which ribosome translating the tag directly participates in the expression of a target gene is low, or mutual confliction (interference between ribosome translating the tag and ribosome translating the gene). That is, it was confirmed that the problem is not a problem related with effectiveness of the tag, through control group test.

[Example 13] Analysis of Effect for Simultaneous Application of Commercially Available Tags and Ramp Tag In the present Example, there is provided a method of using the ramp tag together with typically known tags or fusion proteins for different purposes. The ramp tags were fused together with tags such as His-tag, T7-tag, S-tag, Flag-tag, HA-tag, V5 epitope, Strep-tag, Nano-tag, SBP-tag, c-myc-tag, PelB, Xpress epitope to induce protein expression. In addition, the ramp tag was fused with frequently used fusion proteins such as GST, MBP, NusA, CBP, GFP, Thioredoxin, Mistic, Sumo, DSB, and protein expression was analyzed. As a result, increase in expression amounts due to the ramp tags was confirmed without interfering the role of the typical tag or the fusion protein performing special functions for solubility, detection, localization. Functional evaluation was conducted by mounting his-tag and PelB to a difficult to express protein (β-glucosidase, SmGlu), and fusing the ramp tag therewith. The used ramp tags were the same as Example 7 above.

[Example 14] Analysis of Effect for Sequence Combination of Ramp Tag

In the present Example, there is provided a method of combining ramp tag sequences with respect to the target protein in various orders to be used. Protein over-expressions were confirmed in both of the ramp tags applied to the same target proteins in Example 11, such that it was expected that the ramp tag sequences were usable by combination in various orders. On the basis of the above results, ramp tag sequences of which over-expression was confirmed were combined as shown in Table 10 and it was confirmed whether protein amounts were increased. The used target protein was a difficult to express interleukin-32, and a combination effect was verified. Expression amounts were increased 2.2-3.6 times or more as compared to the control group with which the tag was not fused (FIG. 14).

As a result, it was observed that expression amount was clearly increased as compared to the control group, such that it was confirmed that an effect of increasing translation efficiency was maintained even though the order of the ramp tag sequences was changed. It shows possibility of sequence combination which is possible to function as a universal tag according to circumstances as well as a specific protein optimized tag.

TABLE 10

Ramp tag sequence for gene expression

| Gene | Gene with tag | Ramp tag sequence |
| --- | --- | --- |
| IL32β | R1-IL32β | CTTACACTTACAGGGATAGGGATATACTCGTAC (Sequence 25) |
|  | R2-IL32β | GGGTCGGGGTCGCTTACACTTACATACATATAC (Sequence 26) |
|  | R3-IL32β | TACATATACATAGGGACAGGGACACTTTCGCTT (Sequence 27) |

[Example 15] Analysis of Effect for Sequence Length of Ramp Tag

In the present Example, there is provided a method of inducing over-expression by controlling sequence length of the ramp tag and an effect thereof. Since kinds and appearance frequency of rare codons included in each target protein are different from each other, sequence length of the customized ramp tag may be organically changed. For example, when the appearance frequency of the rare codons included in the target protein is large, the number of ramp codons to be applied is increased to increase the sequence length. In addition, even at the time of combining the sequence orders of the ramp tags in Examples 11 and 14, the expression amount was increased, and therefore, it was expected that the sequence length of the ramp tag was capable of being controlled according to the target protein. On the basis of the above results, it was confirmed whether the protein amount was increased by decreasing or increasing the sequence length of the ramp tag in which the over-expression was confirmed, with the codon unit shown in Table 11. Here, the used target protein was neopullulanase (BCN), activity thereof was measured, and an effect was verified by SDS-PAGE. As a result, expression amounts were increased 1.6-2.7 times or more as compared to the control group with which the tag was not fused. Accordingly, it was confirmed that even though the sequence length of the ramp tag was controlled, an effect of increasing the translation efficiency was maintained.

TABLE 11

Variable Ramp tag sequence for gene expression

| Gene | Gene with tag | Ramp tag sequence |
| --- | --- | --- |
| BCN | R1-BCN | GTGTGCGTGTGCCAGTGTCAGTGTGTCCGG (Sequence 28) |
|  | R2-BCN | GTGTGCGTGTGCCAGTGTCAGTGT (Sequence 29) |
|  | R3-BCN | GTGTGCGTGTGCCAGTGT (Sequence 30) |

[Example 16] Effect Obtained by Applying Protease Recognition Site for Separation of Fused Ramp Tag In the present Example, there is provided a method of removing the tag from the target protein expressed by the ramp tag. The ramp tag was fused together with lgA-protease, granzyme B, Tev protease, prescission protease, thrombin, a factor Xa, or enterokinase recognition and cleavage site as the cleavage sites, and protein expressions were analyzed. Functional evaluation was conducted by mounting cleavage site sequence of prescission protease, thrombin, a factor Xa on the difficult to express cytolysin A (ClyA), and fusing the ramp tag therewith. Here, in order to confirm whether protein expression and tag cleavage were achieved using purified protein by western blot, HIS-tag was attached to C-terminal of ClyA gene. The used cleavage site sequences were shown in Table 12, and the ramp tag was the same as Example 7. As a result, it was confirmed that an increase in expression amounts due to the ramp tag was maintained, and it was observed that it was possible to efficiently remove the ramp tag by the cleavage site (FIG. 15).

TABLE 12

Protease cleavage site sequence fused with ramp tag

| Protease | | Sequence |
| --- | --- | --- |
| Thrombin | Amino Acid | Leu Val Pro Arg$^a$ Gly Ser |
|  | Base | CTG GTT CCG CGT⁻ GGA TCC |
| Factor Xa | Amino Acid | Ile Glu Gly Arg ⁻Gly |
|  | Base | ATC GAA GGT CGT ⁻GGG |
| PreScission Protease | Amino Acid | Leu Glu Val Leu Phe Gln ⁻Gly Pro |
|  | Base | CTG GAA GTT CTG TTC CAG ⁻GGG CCC |

$^a$protease cleavage site

[Example 17] Co-Expression Effect of Multiple Gene by Ramp Tag

In the present Example, there is provided a method of utilizing the ramp tag in a method of producing a specific product with high efficiency from a host cell by over-expressing several enzymes in operon or cluster form in-vivo. There are many cases in which a number of industrial fermentation or biotransformation products are obtained by two or more enzyme activities in a production process. In order to mass-produce the products in the biological system, a method of over-expressing some or all the enzymes in metabolic pathways by operon mode is generally used. In the present Example, biosynthesis efficiency of the target product was confirmed by fusing the ramp tag with two targeted enzymes used for this purpose. The used simultaneous targeted enzymes were 1-deoxy-D-xylulose-5-phosphate synthetase (dxs) and IPP isomerase (idi) that biosynthesize isoprenoid, and the ramp tag was produced by Examples 1 and 2 and effects thereof were verified. As a result, expression amounts of each produced recombinant enzyme were increased 2.2-3.7 times or more as compared to the control group with which the tag was not fused (FIG. 16A). Lycopene content which increased by over-expression inducing effect of the ramp tag was measured and verified by the following method.

Dry cell weight was calculated by performing centrifugation on E. coli culture at 7,000 rpm for 3 minutes, and washing the harvested products once with PBS buffer, and using cell pellets centrifuged at 7,000 rpm for 3 minutes again. To this end, the cell pellets were dried overnight at 105° C. and weighed. In order to determine the lycopene content of the cells, E. coli cells were harvested by centrifugation at 13,000 rpm for 3 minutes, and washed once with PBS buffer. The prepared cells were suspended in acetone (200 ml), and the reaction was induced for 15 minutes at 55° C. under dark condition. The sample was centrifuged again at 13,000 rpm for 10 minutes, and acetone supernatant containing lycopene was transferred to a clean tube. Lycopene content of the extract was quantified by measuring absorbance at 470 nm using a spectrophotometer (Shimadzu) and comparing with lycopene standard samples (Sigma). Standard deviations were in the range of ±5.7% of the measured values. Yield was increased 2.7 times or more as compared to the control group which was not fused with the tag (FIG. 16B).

As a result, a noticeable increase in protein expression amount and an increase in yield of lycopene product in a recombinant strain containing the construct fused with the tag were confirmed as compared to the control group, such that it was confirmed that expression of multiple genes by the ramp tag was also effective. Accordingly, it could be appreciated that the ramp tag of the present invention could be widely utilized for effective metabolite production or establishment for artificial metabolic pathways.

[Example 18] Expression-Inducing Effect of Ramp Tag on Esterase 1767 Gene in Yeast In the present invention, the ramp tag is usable for target gene over-expression in eukaryotes as well as prokaryotes. Saccharomyces cerevisiae was selected as a host cell, and difficult to express protein, esterase 1767, was selected as a target gene. A method of collecting rare codons in codon usage of yeast was performed by the same method as Example 1. Results thereof were shown in Table 13. The ramp tag for the esterase 1767 was configured as described in Example 2 to obtain the following sequences (Table 14). On the basis of the above-description, a primer was produced so as to include the ramp tag in a forward direction while adding a start codon ATG, positioned at N-terminal of esterase 1767 gene. Then, the gene was amplified by PCR and treated with restriction enzymes, and then inserted into a shuttle vector pYES2 having GAL2 promoter. A host was transformed with the prepared recombinant vector by electroporation, and then cultured in a uracil-deficient medium.

In order to confirm expression amounts of the target gene, expression was induced by 2% (v/v) galactose, and was confirmed by western blot. As a result, it was confirmed that 1767 (RY-1767) fused with the ramp tag was over-expressed as compared to the control group showing difficult to expression (FIG. 17). From the above results, it was confirmed that the ramp tag enabled over-expression of industrially useful esterase in eukaryotes, and the ramp tag was usable for mass production of drug proteins that are important for applications in a human.

TABLE 13

Rare codons collected yeast

<2 Box tRNA Sets>

| AA | | Codon | Frequency | tRNA |
|---|---|---|---|---|
| H | His | CAC | 0.87 | 10 |
| C | Cys | UGC | 0.72 | 15 |

<4 Box tRNA Sets>

| AA | | Codon | Frequency | tRNA |
|---|---|---|---|---|
| A | Ala | GCG | 0.9 | 7 |
| G | Gly | GGC | 0.92 | 23 |
| P | Pro | CCC | 0.53 | |
| | Pro | CCG | 0.86 | 5 |
| T | Thr | ACG | 0.77 | 6 |
| V | Val | GUA | 0.99 | 7 |

<6 Box tRNA Sets>

| AA | | Codon | Frequency | tRNA |
|---|---|---|---|---|
| S | Ser | UCG | 0.93 | 4 |
| R | Arg | CGC | 0.38 | — |
| | | CGG | 0.49 | 4 |
| | | CGA | 0.63 | 6 |
| L | Leu | CUG | 0.98 | 3 |
| | | CUA | 0.99 | 10 |

TABLE 14

Ramp tag sequence for 1767 gene expression in yeast host

| Gene | Gene with tag | Ramp tag sequence |
|---|---|---|
| 1767 | RY-1767 | CTACGACTACGATCCTGTTCCTGTGCTCTCGCT (Sequence 28) |

[Example 19] Effect of Ramp Tag on B3(Fv)PE38 Gene in Chinese Hamster Ovary Cell (CHO Cell In the present Example, it was verified that the ramp tag was usable for over-expression induction of the target gene in an animal cell. For analysis of rare codons, codon usage was searched targeting Cricetulus griseus, and for analysis of tRNA genes, C. griseus cell line CHO-K1 was used. A method of collecting the rare codons was performed by the same method as Example 1. Results thereof were shown in Table 16. The ramp tag for B3(Fv)PE38 was configured as described in Example 2 to obtain the following sequences (Table 15). p3×Flag-CMV-7.1 was used as an expression vector, and the gene was cloned by PCR method so as to be positioned at the back of a CMV promoter using a ramp tag primer with a start codon ATG added thereto. Here, as the control group for comparing with the ramp tag in view of an expression-inducing effect, a synthetic gene which was codon optimized (sB3Fv) with wild-type gene was used. In order to transform a host cell CHO-K1 with a plasmid, calcium phosphate mediated transfection was performed. Gibco's CD CHO medium containing 10% fetal bovine serum as a medium was used, and penicillin-streptomycin was used as a selection marker. Cells in an amount up to $5 \times 10^5$ cells/ml were cultured under suspension culture condition, and recovered. Then, western blot was performed using an antibody specific for FLAG. As a result, it was difficult to detect expression of gene which was codon optimized (sB3Fv) by general logic, and it was confirmed that protein amount of B3(Fv)PE38 fused with the ramp tag at N-terminal was increased about 1.5 to 2.1 times as compared to the control group (FIG. 18). Here, beta-actin was used as a protein expression marker.

TABLE 15

Rare codons collected in animal cell *C. griseus*

| Gene | Gene with tag | Ramp tag sequence |
|---|---|---|
| B3(Fv)PE38 | RC-B3Fv | AACTTAAACT TAGTTTGTGT TTGTAGTCGC AGTCGC (SEQ ID NO: 29) |

TABLE 16

Ramp tag sequence for B3(Fv)PE38 gene expression in *C.griseus* host

| Gene | Gene with tag | Ramp tag sequence |
|---|---|---|
| B3(Fv)PE38 | RC-B3Fv | AACTTAAACTTAGTTTGTGTTTGTAGTCGCAGTCGC (Sequence 29) |

[Example 20] Effect of Ramp Tag on B3(Fv)PE38 Gene in Mouse Embryonic Fibroblast Cell (NIH 3T3 Cell In the present Example, it was verified that the ramp tag was usable for over-expression induction of the target gene in an animal cell. For rare codon analysis to be introduced into the tag, the codon usage was inferred by using *Cricetulus griseus* cell line with sufficiently known genetic information, and the same strategy was utilized even for tRNA gene analysis. In addition, the pre-reported NIH 3TS cell information was also systematically integrated to be used. A method of collecting the rare codons was performed by the same method as Example 19. According to the strategy, rare codon analysis results that are significantly similar to Table 15 were obtained. The ramp tag for B3(Fv)PE38 was configured as described in Example 2 to obtain the following sequences (Table 17). p3×Flag-CMV-7.1 was used as an expression vector, and the recombinant gene was cloned so as to be positioned at the back of a CMV promoter using a ramp tag primer with a start codon ATG added thereto by the same method as Example 19. As a control group, codon-optimized gene (sMB3Fv) synthesized with a wild type gene by a typical method was used. In order to transform a host cell NIH 3T3 with a plasmid, calcium phosphate mediated transfection was performed, and Gibco's medium containing 10% fetal bovine serum and penicillin-streptomycin added thereto was cultured in the medium. Cells in an amount up to $5 \times 10^5$ cells/ml were cultured under suspension culture condition, and recovered. Then, western blot was performed using an antibody selective for FLAG. As a result, it was confirmed that the codon optimized (sMB3Fv) gene had difficulty in expression, and it was confirmed that protein expression amount of B3(Fv)PE38 fused with the ramp tag at N-terminal was increased about 2.6 times or more (FIG. 19), similar to the results of Example 19.

TABLE 17

Ramp tag sequence for B3(Fv)PE38 gene expression in *C.griseus* host

| Gene | Gene with tag | Ramp tag sequence |
|---|---|---|
| B3(Fv)PE38 | RM-B3Fv | CTTTGTCTTTGTGAGCGTGAGCGT (Sequence 30) |

[Example 21] Effect of Ramp Tag on Asparaginase B(ansB) Gene in Human Cell

In the present Example, there is provided a method of using the ramp tag for over-expression induction of a target gene in a human cell. Codon usage and tRNA gene were analyzed targeting *Homo sapiens* (hg18—NCBI Build 36.1 Mar. 2006) for analysis of rare codons. A method of collecting the rare codons was performed by the same method as Example 1. As a result, rare codon analysis results were shown in Table 18. The ramp tag with respect to ansB was configured as described in Example 2 to obtain the following sequences (Table 19). p3×Flag-CMV-7.1 was used as a recombinant gene expression vector, and the gene was cloned by PCR method so as to be positioned at the back of a CMV promoter using a ramp tag primer with a start codon ATG added thereto. HEK 293t was used as a human cell line for protein expression, Hyclone's medium DMEM (Dulbecco's modified eagle medium) containing 10% fetal bovine serum added thereto was used as a medium, and penicillin-streptomycin was used as a selection marker. Cells in an amount up to $5 \times 10^5$ cells/ml were cultured under suspension culture condition, and recovered. Then, western blot was performed using an antibody specific for ansB. As a result, it was confirmed that ansB (RH-ansB) protein fused with the ramp tag was over-expressed (7.2-10.5 times or more) as compared to the control group exhibiting significantly low expression yield (FIG. 20). In order to evaluate protein expression, comparison was made by performing western blot using an antibody specific for beta-actin. Incidentally, as a result obtained by inducing expression of fluorescent protein mBFP which was significantly difficult to be expressed in eukaryotes, in the same cell line, using the same strategy, it was confirmed that over-expression was achieved in fluorescent protein mBFP. Here, an expression amount was increased 1.7 to 3.5 times or more, and in the quantitative evaluation process, an antibody specific for mBFP was used, and actin genes and protein were used as the control group for comparison.

TABLE 18

Rare codons collected in human cell

<4 Box tRNA Sets>

| | AA | Codon | Frequency | tRNA |
|---|---|---|---|---|
| A | Ala | GCG | 0.74 | 5 |
| P | Pro | CCG | 0.69 | 4 |
| T | Thr | ACG | 0.61 | 6 |
| V | Val | GUA | 0.71 | 5 |

<6 Box tRNA Sets>

| | AA | Codon | Frequency | tRNA |
|---|---|---|---|---|
| S | Ser | UCG | 0.44 | 4 |
| R | Arg | CGU | 0.45 | 7 |
| | | CGA | 0.62 | 6 |
| L | Leu | CUA | 0.72 | 3 |
| | | UUA | 0.77 | 7 |

<3 Box and other tRNA Sets>

| | AA | Codon | Frequency | tRNA |
|---|---|---|---|---|
| I | Ile | AUA | 0.75 | 5 |

TABLE 19

Ramp tag sequence for ansB gene expression in H. sapiens host

| Gene | Gene with tag | Ramp tag sequence |
|---|---|---|
| AnsB | RH-ansB | CCATTACCATTATGCCGTTGCCGTACAACG (Sequence 31) |

[Example 22] Effect of Ramp Tag on Neopullulanase (BCN) Gene in Plant Cell

In the present Example, it was verified that the ramp tag was usable for over-expression induction of the target gene in a plant cell. Codon usage and tRNA gene analysis were conducted targeting *Arabidopsis thaliana* (GenBank sequences) for analysis of rare codons for ramp tag for the purpose of target gene expression. A method of collecting the rare codons was performed by the same method as Example 1. As a result, rare codon analysis results were shown in Table 20. The ramp tag with respect to BCN was configured as described in Example 2 to obtain the following sequences (Table 21). 326-GFP (ABRC, Ohio State University, USA) was used as an expression vector, and the gene was cloned by PCR method so as to be positioned at the back of a 35S promoter using a ramp tag primer with a start codon ATG added thereto. In order to transform a host cell with a plasmid, PEG-mediated transformation was used, and transformed cells were cultured for 24 hours in an artificial environment room of 23° C. Then, a protein extract solution (10 mM HEPES, pH 7.5, 10 mM NaCl, 3 mM $MgCl_2$, 5 mM DTT, 5 mM EDTA, 0.2% TritonX-100) was added to the protoplast to induce a reaction at 4° C. for 1 hour, followed by centrifugation at 4° C. at 13,000 rpm for 10 minutes to separate the precipitate with the supernatant. Then, protein extract of the supernatant was developed by SDS-PAGE, and western blot was performed using anti-GFP antibody (monoclonal anti-GFP antibody, Clontech). In combination with this, functional expression amount was calculated by a typical activity measurement of BCN. As a result, it was confirmed that expression amounts of BCN protein fused with the ramp tag at N-terminal were increased about 2.4-3.1 times or more as compared to the control group. From the above results, it was confirmed that the ramp tag was also effectively usable for protein expression system using bacteria, yeast, animal cells, and plant cells, as hosts.

TABLE 20

Rare codons collected in plant A. thaliana

<2 Box tRNA Sets>

| | AA | Codon | Frequency | tRNA |
|---|---|---|---|---|
| H | His | CAC | 0.87 | 10 |
| C | Cys | UGC | 0.72 | 15 |

<4 Box tRNA Sets>

| | AA | Codon | Frequency | tRNA |
|---|---|---|---|---|
| A | Ala | GCG | 0.9 | 7 |
| G | Gly | GGC | 0.92 | 23 |
| P | Pro | CCC | 0.53 | |
| | Pro | CCG | 0.86 | 5 |
| T | Thr | ACG | 0.77 | 6 |
| V | Val | GUA | 0.99 | 7 |

<6 Box tRNA Sets>

| | AA | Codon | Frequency | tRNA |
|---|---|---|---|---|
| S | Ser | UCG | 0.93 | 4 |
| R | Arg | CGC | 0.38 | |
| | | CGG | 0.49 | 4 |
| | | CGA | 0.63 | 6 |
| L | Leu | CUG | 0.98 | 3 |
| | | CUA | 0.99 | 10 |

TABLE 21

Ramp tag sequence for BCN gene expression in plant host

| Gene | Gene with tag | Ramp tag sequence |
|---|---|---|
| BCN | RP-BCN | AGGCTGAGGCTGCAGTGCCAGTGC (Sequence 32) |

[Example 23] Effect of Expression Induction of Ramp Tag on Antibody Protein

The efficacy of the above-described ramp tag was applied to an antibody protein with high value-added for medical purpose. Antibody proteins, anti-CD20 (anti-B-lymphocyte antigen CD20) and anti-TNFα (anti-tumour necrosis factor alpha) have significantly broad availability as medical treatment candidates for Non-Hodgkin's lymphoma, rheumatoid arthritis, and the like; however, have a disadvantage in that mass production is difficult to be performed by typical methods. At the time of producing the ramp tag with these proteins and measuring expression amounts in an animal cell host, noticeable increase in protein amounts and increase in activity were confirmed as compared to the control group. The antibody genes were produced by a synthesis method disclosed in the known documents (U.S. Pat. No. 8,599,226; U.S. 60/223,360), and expression and activity of the antibody were confirmed by a typical method. Purity of the purified anti-CD20 was confirmed by SDS-PAGE gel electrophoresis, and affinity and specificity of the antibody were compared with those of the control group, 2B8. When comparing anti-CD20 antibody tested for direct and competitive binding assays with an anti-CD20, monoclonal antibody 2B8 of a rat, affinity and specificity comparable to a number of CD20 positive B cell lines were verified (data were not shown). An apparent affinity constant of the antibody (Kap) was measured by the direct coupling of anti-CD20 which was radiation-labeled with $I^{125}$, and was compared with that of 2B8 which was labeled by the same method. Kap theoretical value of anti-CD20 produced by CHO was $4.2 \times 10^{-9}$ M, and Kap theoretical value of antibody 14/59 produced by SP2/0 was $6.7 \times 10^{-9}$ M. Kap theoretical value of 2B8 was $3.5 \times 10^{-9}$ M. Specificity and immunoreactivity of the antibody were confirmed by comparing with 2B8 in view of an effective competition ability by using direct competition with radiation immunoassay. In addition, an amount in which anti-TNF was present was detected by anti-human IgG Fc ELISA. In briefly, various dilutions of the cell supernatant were cultured in 96-well EIA plates coated with polyclonal goat anti-human IgG Fc fragment, and then the bound human IgG was detected by using alkaline phosphate-conjugated goat anti-human IgG (H+L) and appropriate color substrates. In order to use a standard curve using the same purified mAb measured in the cell supernatant as a standard material, human IgG in supernatant was included for each EIA plate.

Here, the ramp tag sequences used for inducing expression of these proteins were shown in Table 22 below.

TABLE 22

Ramp tag sequences for antibody protein gene expression

| Gene | Gene with tag | Ramp tag sequence |
|---|---|---|
| CD20 | RL-CD20 | TACACGTACACGAAAGCGAAAGCG (Sequence 33) |
|  | RH-CD20 | GATTGTGATTGTAAGCGTAAG (Sequence 34) |
| TNF | RL-Alpha | CATGCGCATGCGTACTTATAC (Sequence 35) |
|  | RH-Alpha | AACCGTAACCGTGATTGTGATTGT (Sequence 36) |

As a result, it shows that the ramp tag according to the present invention is customized and designed according to the target gene to be directly usable for antibody production.

[Example 24] Effect of Ramp Tag on Interaction Between Substrate and Protein

In the present Example, there is provided a method of improving bonding force between the substrate and the protein by using the ramp tag to increase activity. As an example, when metal affinity is increased by controlling charge value of the ramp tag amino acid sequence of the invention (intensive arrangement of rare codons encoding histidine or acidic amino acid), it is expected that metal ions acting as a coenzyme or a structural stabilizer may be smoothly supplied to increase activity of metal-dependent enzyme (metallo-enzyme). On the basis of this hypothesis, whether or not antibiotic resistance of strain is increased was tested by using antibiotic resistant protein beta-lactamase. A metallo-β-lactamase (MBL) series of beta-lactamase, carbapenemase, is requiring $Zn^{2+}$ for enzymatic activity. On the basis of this, the ramp tags were produced with negatively charged group of amino acids or imidazole group of amino acid, and effects thereof were verified. MBL selected as the target was prepared by cloning VIM2 gene of *pseudomonas aeruginosa* into a pET vector. After pET-VIM2 was introduced into *E. coli* BL21 (DE3), expression was induced by IPTG, and each concentration of imipenem was added thereto to thereby confirm antibiotic resistance. Whether enzymatic activity was changed by charged rare codons arranged in the ramp tag was analyzed by comparing resistance degree shown by whether $Zn^{2+}$ was added or not added in the minimum nutrient medium (M9) having a composition of 5×M9 salt solution (48 mM $Na_2HPO_4$-$7H_2O$, 22.0 mM $KH_2PO_4$, 8.6 mM NaCl, 18.7 mM $NH_4Cl$), and 2 mM $MgSO_4$, 0.1 mM $CaCl_2$. The used ramp tag sequences were shown in Table 23 below. As a result, it could be confirmed that protein expression and activity of VIM2 (RN1-VIM2, RN2-VIM2) fused with the ramp tag were increased 2.6-4.2 times or more as compared to the control group (VIM2), and it was confirmed that when $Zn^{2+}$ was not added to the minimum nutrient medium, activity thereof was not significantly different from that of the control group; however, when 5 mM $Zn^{2+}$ was added, an antibiotic resistance activity of negatively charged ramp tags (RN1-VIM2, RN2-VIM2) was increased 1.8-2.4 times or more as compared to positively charged ramp tags (RP1-VIM2, RP2-VIM2). As a result, it was confirmed that the ramp tag with a chelating effect was usable by observing noticeable increase in expression and activity as compared to the control group (FIG. 21). Accordingly, it shows that affinity required for binding to a specific substrate in cells was increased by the ramp tag to improve opportunity of catalytic reaction. In addition, when the ramp tag is designed in a way to mimic the specific peptide required for interaction, binding force between proteins may be affected to control the interaction.

TABLE 23

Ramp tag sequence for gene expression

| Gene | Gene with tag | Ramp tag sequence |
|---|---|---|
| VIM2 | RN1-VIM2 | GACTGCGACTGCCATACTCATACTGAA (Sequence 37) |
|  | RN2-VIM2 | GATCACGATCACGAGTCAGAGTCACAT (Sequence 38) |
|  | RP1-VIM2 | AAGTGTAAGTGTCGCCGACGCCGA (Sequence 39) |
|  | RP2-VIM2 | AAACGGAAACGGCATAGACATAGACGT (Sequence 40) |

[Example 25] Effect of Over-Expression Induction and Effect of Purification of Ramp Tag Arranged with Histidine Rare Codon In the present Example, there is provided a method of simultaneously performing target protein expression and purification with high-efficiency by the ramp tag. In the method for collecting the rare codons, as shown in Example 1, histidine is decoded by a rare codon (CAC) capable of improving difficult to expression of the target protein, and has an imidazole ring in a structure to provide metal ion affinity. Therefore, when configuring the codons into the ramp tag, expression problem of the complex-expression protein could be overcome and purification using affinity chromatography could also simultaneously be performed. In configuring a sequence of the ramp tag based on the assumption, histidine rare codon sequence was combined as shown in Table 24, and an effect of over-expression induction and an effect of purification were confirmed. The used target protein was blue fluorescent protein (mBFP), and purified by the following method using Ni-NTA. After culturing a single colony transformed by the same method as Example 3 using the recombinant vector produced in the present Example, recovered cells were suspended in 50 ml binding buffer (20 mM Tris-HCl, 500 mM NaCl, pH 7.5). Then, the cells were disrupted by repeating a process 10 times, the process including applying ultrasonic waves at a low temperature for 10 seconds using a sonicator and allowing the cells to stand for 30 seconds. After the disrupted cells were subjected to centrifugation (15,000 rpm, 10 mins) at a high speed to remove insoluble precipitate, supernatant including soluble proteins was recovered. After cell debris remover (CDR) (1 g per 20 ml) was added to macromolecules such as chromosome, polysaccharide, and the like, present in the recovered supernatant to induce a precipitation, impurities were removed by centrifugation with the above-described method or by 0.45 μm of syringe filter. The supernatant from which the impurities were removed was diluted by adding a binding buffer with volume increased by 10 times. Ni-NTA resin used for affinity chromatography was thoroughly cleaned with 50 ml of binding buffer to reach equilibrium. To the equilibrium resin, a protein solution was applied to be bound at a rate of 2 ml/min, and then non-bound proteins and non-specifically and weakly bound impurities were removed by flowing 100 ml of wash buffer (20 mM Tris-HCl, 500 mM NaCl, 10 mM imidazole, pH 7.5) at a flow rate of 3 ml/min. Elution of the protein was performed by flowing an elution buffer (20 mM Tris-HCl, 500 mM NaCl, 250 mM imidazole, pH 7.5) at a rate of 5 ml/min. A collected fraction including recovered fluorescent proteins was confirmed by fluorescence-based sensitivity analysis, and sodium chloride which was added into the elution buffer so as to reduce non-specific protein interactions with imidazole was removed by a cut-off size 10 kDa filter. As a result obtained by confirming the protein by SDS-PAGE, the expression amount was increased 2.2 to 3.7 times or more as compared to the control group that was not fused with the tag. As confirmed in FIG. 22B, protein with purity of 90% or more could be recovered by a single process due to binding of histidine periodically arranged in the ramp tag to the specific resin Ni-NTA. In addition, it was confirmed that fluorescent value was similarly measured regardless of the presence or the absence of the tag, such that there was no problem even in activity of the recombinant protein.

TABLE 24

Ramp tag sequences for gene over-expression and purification, including histidine rare codon

| Gene | Gene with tag | Ramp tag sequence |
|---|---|---|
| BFP | RH1-BFP | CTCCACGGTCACCAATGCTATCACTACCAC (Sequence 41) |
| | RH2-BFP | GTACGGGTACACAGTCACAGTCGGCATCGACATCGA (Sequence 42) |

As a result, a significant increase in expression amounts was observed as compared to the control group, and it was confirmed that purification with high purity was capable of being performed by using the ramp tag, without interfering protein activity. Therefore, it was confirmed that affinity binding according to purposes was capable of being induced by systematically combining rare codons encoding specific amino acids included in the ramp tag.

The invention claimed is:

1. A method of producing a nucleic acid expression vector comprising a first nucleic acid sequence encoding a target protein (target gene sequence) and a second nucleic acid sequence encoding a ramp tag sequence, said method comprising:
   (a) identifying rare codons of a host cell by determining a frequency of usage of codons by the host cell and a number of isoacceptor tRNA of codons of the host cell, wherein the rare codons have the frequency of usage of the codons of 0.5 to 3% and the number of isoacceptor tRNA of 0 to 2;
   (b) determining which of the rare codons identified in (a) is appeared in the target gene sequence;
   (c) identifying a preferred codon which appears in the target gene sequence with a frequency of greater than 2%;
   (d) providing the ramp tag sequence comprising more than one rare codons and containing the preferred codon between the individual rare codons; and
   (e) producing the nucleic acid expression vector comprising the target gene sequence and the second nucleic acid sequence,
   wherein the ramp tag sequence contains 1-20 codons.

2. The method of claim 1, wherein (b) comprises determining a frequency and a position of the rare codons of (a) in the target gene sequence, and wherein the ramp tag sequence has a rare codon of the lowest frequency in the target gene sequence, at its 5'-end.

3. The method of claim 1, wherein the host cell is selected from the group consisting of E. coli, yeast, a Chinese hamster ovary cell, a human cell, and a plant cell.

4. The method of claim 3, wherein the host cell is selected from the group consisting of E. coli K-12, Saccharomyces cerevisiae, CHO-K1, HEK 293t, and 326-GFP.

5. The method of claim 1, wherein the target gene sequence encodes a peptide selected from the group consisting of an esterase, β-glucosidase, cytolysin A (ClyA), recombinant antibody (single chain Fv: scFv), asparaginase B, tetra-cell adhesion molecule (T-CAM), B3(Fv)PE38, chloramphenicol acetyltransferase (CAT), neopullulanase, interleukin-1, interleukin-32, anti-B-lymphocyte antigen CD20 (anti-CD20), and anti-tumor necrosis factor alpha (anti-TNFα).

6. An expression vector to express an exogenous target protein in a host cell, said expression vector comprises a first nucleic acid sequence encoding the exogenous target protein (an exogenous target gene sequence) and a second nucleic acid sequence encoding a ramp tag sequence,
   wherein the ramp tag sequence comprises a rare codon of the host cell, said rare codon having a frequency of codon usage of 0.5 to 2% and a number of isoacceptor tRNA of 0 to 2, and said rare codon being also present in the exogenous target gene sequence,
   wherein the ramp tag sequence is selected from the group consisting of SEQ ID NOS: 1 to 3, 5, 6, and 11 to 45.

7. A method of increasing an expression efficiency of an exogenous target protein in a host cell, comprising:
   transforming the host cell with the expression vector of claim 6; and
   culturing the transformed host cell in a culture medium that is suitable for expressing the exogenous target protein.

8. The method of claim 7, wherein the ramp tag sequence of the expression vector comprises more than one rare codons and contains a preferred codon between the individual rare codons, said preferred codon being a codon which appears in the exogenous target gene with a frequency of greater than 2%.

9. The method of claim 7, wherein the host cell is selected from the group consisting of E. coli K-12, Saccharomyces cerevisiae, CHO-K1, HEK 293t, and 326-GFP.

10. The method of claim 7, wherein the exogenous target protein is selected from the group consisting of esterase, β-glucosidase, cytolysin A, single chain Fv: scFv, asparaginase B, tetra-cell adhesion molecule, B3(Fv)PE38, chloramphenicol acetyltransferase, neopullulanase, interleukin-1, interleukin-32, anti-B-lymphocyte antigen CD20, and anti-tumor necrosis factor alpha.

11. The method of claim 7, wherein the ramp tag sequence is positioned so as to be fused to the 5' end or the 3' end of the exogenous target gene sequence, or positioned apart from the target gene so as to be independently translated from the exogenous target gene.

12. The method of claim 7, wherein the expression vector further comprises an additional tag selected from the group consisting of His tag, T7 tag, S-tag, Flag-tag, HA-tag, V5 epitope, PelB, and Xpress epitope.

13. The method of claim 12, wherein the expression vector further comprises a third nucleic acid sequence encoding an additional protein which forms a fusion protein with the exogenous target protein, said addition protein being selected from the group consisting of glutathione S-transferase (GST), maltose binding protein (MBP), transcription termination and antitermination (NusA), CREB binding protein (CBP), green fluorescent protein (GFP), thioredoxin, mistic, sumo and Disulfide-bond isomerase (DSB).

14. A method of separating a target protein from a culture solution containing the target protein and impurities, comprising:
   allowing the culture solution pass through an affinity chromatography so as the target protein to bind to the affinity chromatography; and
   eluting the target protein from the affinity chromatography,
   wherein the target protein is expressed from the expression vector of claim 6,
   wherein the ramp tag sequence of the expression vector is coupled to a histidine rare codon affinity chromatography.

15. The method of claim 14, wherein the affinity chromatography employs Ni-NTA resin to which a histidine residue binds, said histidine residue being encoded by the histidine rare codon.

16. The expression vector of claim 6, which further comprises a protein cleavage site-encoding sequence, said protein cleavage site-encoding sequence being placed between the ramp tag sequence and the exogenous target gene sequence.

17. The expression vector of claim 16, wherein the protein cleavage site is a peptide sequence recognized by an enzyme selected from the group consisting of IgA-protease, granzyme B, Tev protease, prescission protease, thrombin, a factor Xa, or enterokinase.

18. A host cell comprising the expression vector of claim 6.

19. The expression vector of claim 6, wherein the ramp tag sequence has a rare codon of the lowest frequency of codon usage at its 5'-end.

20. The expression vector of claim 6, wherein the ramp tag sequence comprises more than one rare codons and contains a preferred codon between the rare codons, said preferred codon being a codon which appears in the exogenous target gene with a frequency of greater than 2%.

21. The host cell of claim 18, which is selected from the group consisting of E. coli, yeast, a Chinese hamster ovary cell, a human cell, and a plant cell.

22. The host cell of claim 21, which is selected from the group consisting of E. coli K-12, Saccharomyces cerevisiae, CHO-K1, HEK 293t, and 326-GFP.

23. The expression vector of claim 6, wherein the exogenous target gene encodes a peptide selected from the group consisting of an esterase, (3-glucosidase, cytolysin A, single chain Fv: scFv, asparaginase B, tetra-cell adhesion molecule, B3(Fv)PE38, chloramphenicol acetyltransferase, neopullulanase, interleukin-1, interleukin-32, anti-B-lymphocyte antigen CD20, and anti-tumor necrosis factor alpha.

* * * * *